(12) United States Patent
Holmes et al.

(10) Patent No.: US 10,639,383 B2
(45) Date of Patent: May 5, 2020

(54) METHODS AND COMPOSITIONS FOR ENGINEERING IMMUNITY

(71) Applicant: Sangamo BioSciences, Inc., Richmond, CA (US)

(72) Inventors: Michael C. Holmes, Richmond, CA (US); Brigit E. Riley, Richmond, CA (US)

(73) Assignee: Sangamo Therapeutics, Inc., Richmond, CA (US)

(*) Notice: Subject to any disclaimer, the term of this patent is extended or adjusted under 35 U.S.C. 154(b) by 103 days.

(21) Appl. No.: 15/357,772

(22) Filed: Nov. 21, 2016

(65) Prior Publication Data

US 2017/0196992 A1 Jul. 13, 2017

Related U.S. Application Data

(60) Provisional application No. 62/405,521, filed on Oct. 7, 2016, provisional application No. 62/258,864, filed on Nov. 23, 2015.

(51) Int. Cl.
| | |
|---|---|
| A01N 63/00 | (2020.01) |
| A61K 48/00 | (2006.01) |
| C07K 16/32 | (2006.01) |
| A61K 35/28 | (2015.01) |
| A61P 35/00 | (2006.01) |
| A61P 25/16 | (2006.01) |
| C12N 15/86 | (2006.01) |
| A61K 35/12 | (2015.01) |
| C07K 16/18 | (2006.01) |
| C07K 16/30 | (2006.01) |
| C12N 15/62 | (2006.01) |
| A61K 39/00 | (2006.01) |

(52) U.S. Cl.
CPC .......... *A61K 48/0058* (2013.01); *A61K 35/12* (2013.01); *A61K 35/28* (2013.01); *A61P 25/16* (2018.01); *A61P 35/00* (2018.01); *C07K 16/18* (2013.01); *C07K 16/30* (2013.01); *C07K 16/32* (2013.01); *C12N 15/62* (2013.01); *C12N 15/86* (2013.01); *A01K 2227/105* (2013.01); *A01K 2267/03* (2013.01); *A61K 2039/505* (2013.01); *C07K 2317/622* (2013.01); *C07K 2317/626* (2013.01); *C07K 2319/31* (2013.01); *C12N 2750/14143* (2013.01)

(58) Field of Classification Search
CPC ......... A61K 39/00; A61K 48/00; C12N 15/63
See application file for complete search history.

(56) References Cited

U.S. PATENT DOCUMENTS

| | | |
|---|---|---|
| 5,789,538 A | 8/1998 | Rebar et al. |
| 5,925,523 A | 7/1999 | Dove et al. |
| 6,007,988 A | 12/1999 | Choo |
| 6,013,453 A | 1/2000 | Choo |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case |
| 6,607,882 B1 | 8/2003 | Cox, III et al. |
| 6,689,558 B2 | 2/2004 | Case |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 1,013,219 A1 | 3/2006 | Case et al. |
| 7,067,317 B2 | 6/2006 | Rebar et al. |
| 7,074,596 B2 | 7/2006 | Darzynkiewicz et al. |
| 7,153,949 B2 | 12/2006 | Kim et al. |
| 7,163,824 B2 | 1/2007 | Cox, III et al. |
| 7,262,054 B2 | 8/2007 | Jamieson et al. |
| 7,888,121 B2 | 2/2011 | Urnov et al. |
| 7,914,796 B2 | 3/2011 | Miller et al. |
| 7,951,925 B2 | 5/2011 | Ando et al. |
| 8,034,598 B2 | 10/2011 | Miller et al. |
| 8,110,379 B2 | 2/2012 | DeKelver et al. |
| 8,153,773 B2 | 4/2012 | Jemielity et al. |
| 8,409,861 B2 | 4/2013 | Guschin et al. |
| 8,563,314 B2 | 10/2013 | Gregory et al. |
| 8,586,526 B2 | 11/2013 | Gregory et al. |
| 8,623,618 B2 | 1/2014 | Doyon et al. |
| 8,697,359 B1 | 4/2014 | Zhang |
| 8,703,489 B2 | 4/2014 | Wang |
| 8,771,985 B2 | 7/2014 | Cui et al. |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Hollevoet (2017, J Tansl Med, 15:131, pp. 1-19).*
Papapetrou (2016, Molecular Therapy, 24:678-684).*
Chichili (2013. Protein Science, 22:153-167).*
Senutovitch (2012, Biochemistrty, 51:2471-85).*
Zhao (Sep. 2015, Int J Clin Exp Med, 8:14827-14836).*
Chen (2008. Biochemistry, 73:702-710).*
Qin (2010, Acta Biochim, Biophys Sin, 42:129-136).*
Desplanq (1994, Protein Engineering, 7:1027-1033).*
Auslander, et al., "Rational Design of a Small Molecule-Responsive Intramer Controlling Transgene Expression in Mammalian Cells," *Nucleic Acids Research* 39(22):e155 Published online Oct. 7, 2011 doi:10.1093/nar/gkr829 (2011).
Baker, et al., "Therpeutic Antibody Gene Transfer: An Active Approach to Passive Immunity," *Molecular Therapy* 10(3):411-416 (2004).

(Continued)

*Primary Examiner* — Valarie E Bertoglio
(74) *Attorney, Agent, or Firm* — Pasternak Patent Law

(57) ABSTRACT

Nucleases and methods of using these nucleases for expressing an antibody from a safe harbor locus in a secretory tissue, and clones and animals derived therefrom.

7 Claims, 18 Drawing Sheets

Specification includes a Sequence Listing.

(56) References Cited

U.S. PATENT DOCUMENTS

| | | |
|---|---|---|
| 8,945,868 B2 | 2/2015 | Collingwood et al. |
| 8,956,828 B2 | 2/2015 | Bonini et al. |
| 9,005,973 B2 | 4/2015 | Cost et al. |
| 9,045,763 B2 | 6/2015 | DeKelver et al. |
| 9,150,847 B2 | 10/2015 | Rebar |
| 9,200,266 B2 | 12/2015 | Wang |
| 9,255,250 B2 | 2/2016 | Gregory et al. |
| 9,394,545 B2 | 7/2016 | Rebar |
| 2003/0232410 A1 | 12/2003 | Liljedahl et al. |
| 2005/0026157 A1 | 2/2005 | Baltimore et al. |
| 2005/0064474 A1 | 3/2005 | Umov et al. |
| 2005/0208489 A1 | 9/2005 | Carroll et al. |
| 2006/0063231 A1 | 3/2006 | Li et al. |
| 2006/0188987 A1 | 8/2006 | Gischin et al. |
| 2008/0159996 A1 | 7/2008 | Ando et al. |
| 2008/0299580 A1 | 12/2008 | DeKelver et al. |
| 2009/0068164 A1 | 3/2009 | Segal et al. |
| 2010/0218264 A1 | 8/2010 | Cui et al. |
| 2011/0265198 A1 | 10/2011 | Gregory et al. |
| 2012/0017290 A1 | 1/2012 | Cui et al. |
| 2012/0128635 A1 | 5/2012 | Gregory et al. |
| 2012/0195936 A1 | 8/2012 | Rudolph et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2013/0196373 A1 | 8/2013 | Gregory et al. |
| 2014/0120622 A1 | 5/2014 | Gregory et al. |
| 2015/0056705 A1 | 2/2015 | Conway et al. |
| 2015/0159172 A1 | 6/2015 | Miller et al. |
| 2015/0174169 A1 | 6/2015 | Genovese et al. |
| 2015/0335708 A1 | 11/2015 | Kwak et al. |
| 2016/0024474 A1 | 1/2016 | Cost et al. |
| 2016/0030477 A1 | 2/2016 | Conway et al. |
| 2016/0060656 A1 | 3/2016 | Rebar |
| 2016/0326548 A1 | 11/2016 | Cost |

FOREIGN PATENT DOCUMENTS

| | | | |
|---|---|---|---|
| WO | WO 96/06166 A1 | 2/1996 | |
| WO | WO 98/37186 A1 | 8/1998 | |
| WO | WO 98/53057 A1 | 11/1998 | |
| WO | WO 98/53058 A1 | 11/1998 | |
| WO | WO 98/53059 A1 | 11/1998 | |
| WO | WO 98/53060 A1 | 11/1998 | |
| WO | WO 98/54311 A1 | 12/1998 | |
| WO | WO 00/27878 A1 | 5/2000 | |
| WO | WO 01/60970 A2 | 8/2001 | |
| WO | WO 01/88197 A2 | 11/2001 | |
| WO | WO 02/016536 A1 | 2/2002 | |
| WO | WO 02/077227 A2 | 10/2002 | |
| WO | WO 02/099084 A2 | 12/2002 | |
| WO | WO 03/016496 A2 | 2/2003 | |
| WO | WO 10/079430 A1 | 7/2010 | |
| WO | WO-2014059115 A1 * | 4/2014 | ......... A61K 38/1709 |
| WO | WO2014165506 A1 | 10/2014 | |

OTHER PUBLICATIONS

Beerli, el al., "Engineering Polydactyl Zinc-Finger Transcription Factors," *Nature Biotechnology* 20:135-141(2002).

Beisel, et al., "Design of Small Molecule-Responsive microRNAs Based on Structural Requirements for Drosha Processing," *Nucleic Acids Research* 39(7):2981-2994 (2011).

Beurdeley, et al., "Compact Designer Talens for Efficient Genome Engineering," *Nature Communications* 4:1762 Published online Apr. 23, 2013 doi:10.1038/ncomms2782 (2013).

Bigal, et al., "Safety, Tolerability, and Efficacy of TEV-48125 for Preventive Treatment of Chronic Migraine: A Multicentre, Randomised, Double-Blind, Placebo-Controlled, Phase 2b Study," *Lancet Neurol.* 14(11):1091-1100 (2015).

Boch, et al., "Breaking the Code of DNA Binding Specificity of Tal-Type III Effectors," *Science* 326:1509-1512 (2009).

Bonas, et al., "Genetic and Structural Characterization of the Avirulence Gene AVRBS3 From Xanthomonas Campestris PV. Vesicatoria," *Mol. Gen. Genet.* 218:127-136 (1989).

Caballero, et al., "Cancer/Testis (CT) Antigens: Potential Targets For Immunotherapy," *Cancer Science.* 100(11):2014-2021 (2009).

Chames, et al. "Therapeutic Antibodies: Successes, Limitations and Hopes for the Future," *British Journal of Pharmacology* 157:220-233 (2009).

Choo, et al.," Avannces in Zinc Finger Engineering" *Curr. Opin. Struct. Biol.* 10:411-416 (2000).

Christian, et al., "Targeting DNA Double-Strand Breaks with TAL Effector Nucleases," *Genetics* 186:757-761 Published online Jul. 20, 2010 doi:10.1534/genetics.110.120717 (2010).

Cong, et al., "Multtplex Genome Engineering using CRISPR/CAS Systems," Sciencexpress/10.1126/science.1231143 (2013).

Deal, et al., "Engineering Humoral Immunity as Prophylaxis or Therapy," *Curr. Opin. Immunol.* 35:113-122 (2015).

Gal, et al., "Inhibition of Protease-Inhibitor Resistant Hepatitis C Virus Replicons and Infectious Virus by Intracellular Intrabodies," *Antiviral Res.* 88(1):95-106 (2010) doi:10.1016/k.antiviral.2010.08. 001.

Goswami, et al., "Developments and Challenges for mAb-Based Therapeutics," *Antibodies.* 2:452 (2013).

Goverdhana, et al., "Regulatable Gene Expression Systems for Gene Therapy Applications: Progress and Future Challenges," *Mol. Ther.* 12(2):189-211 (2005) doi:10.1016/j.ymthe.2005.03.022.

Gow, et al., "Safety, Tolerability. Pharmacokinetics, and Efficacy of AMG 403, A Human Anti-Nerve Growth Factor Monoclonal Antibody, in Two Phase 1 Studies With Healthy Volunteers and Knee Osteoarthritis Subjects," *Arthritis Res Ther.* 17:282 (2015).

Guo, et al., "Directed Evolution of an Enhanced and Highly Efficient Foki Cleavage Domain for Zinc Finger Nucleases," *Journal of Molecular Biology* 400(1):96-107 (2010).

Haft, et al., "A Guild of 45 CRISPR-Associated (CAS) Protein Families and Multiple CRISPR/CAS Subtypes Exist in Prokaryotic Genomes,"*PLoS Comput. Biol.* 1(6):474-483 (2005).

Harris, et al., "The Anti-(+)-Methamphetamine Monoclonal Antibody mAb7F9 Attenuates Acute(+):Methamphetamine Effects on Intracranial Self-Stimulation in Rats," *PLOS ONE* doi:10.1371/journal.pone.0118787 (2015).

Heuer, et al., "Repeat Domain Diversity of AVRBS3-Like Genes in Ralstonia Solanacearum Strains and Association With Host Preferences in the Field," *Appl. and Envir. Micro.* 73(13):4379-4384 (2007)

Heusohn, et al. "The Pmed1 Promoter of Human FcγRIIIA Can Function As a NK/T Cell-Specific Restriction Element, Which Involves Binding of Sp1 Transcription Factor," *Journal of Immunology* 168:2857-2864 (2002).

Hirose, et al., "NGF/TrkA Signaling As a Therapeutic Target for Pain," *Pain Practice* 16(2):175-182 (2015).

Hoffman, et al., "Blinatumomab, a Bi-Specific Anti-CD19/CD3 BiTE® Antibody for the Treatment of Acute Lymphoblastic Leukemia: Perspectives and Current Pediatric Applications," *Frontiers in Oncology* 4(64):1-5 (2014).

Hong, et al., "Generation of 1E8 Single Chain Fv-Fc Construct Against Human CD59," *Immune Network.* 12(1):33-39 (2012).

Isalan, et al., "A Rapid, Generally Applicable Method to Engineer Zinc Fingers Illustrated by targeting the HIV-1 Promoter," *Nat. Biotechnology* 19:656-660 (2001).

Jansen, et al., "Identification of Genes That Are Associated With DNA Repeats in Prokaryotes," *Molecular Microbiology* 43(6):1565-1575 (2002).

Jinek, et al., "A Programmable Dual-RNA-Guided DNA Endonuclease in adaptive Bacterial Immunity," *Science* 337:816-821 (2012).

Jo, et al., "Engineering Therapeutic Antibodies Targeting G-Protein-Coupled Receptors," *Exp Mol Med.* 48(2) e207 Published online Feb. 5, 2016 doi: 10.1038/emm.2015.105 (2016).

Kay, et al., "A Bacterial Effector Acts As a Plant Transcription Factor and Induces a Cell Size Regulator," *Science* 318:648-651 (2007).

Kennedy, et al., "Proteen-Responsive Ribozyme Switches in Eukaryotic Cells," *Nucleic Acids Research* 42(19):12306-12321 (2014).

(56) References Cited

OTHER PUBLICATIONS

Kontermann, et al., "Bispecific Antibodies," *Drug Discovery Today* 20(7):838-847 (2015).
Kormann, et al., "Expression of Therapeutic Proteins After Delivery of Chemically Modified mRNA in Mice," *Nature Biolotechnology* 29(2):154-157 (2011).
Liu, et al., "An N-Termlnal Antibody Promotes the Transformation of Amyloid Fibrils Into Oligomers and Enhances the Neurotoxicity of Amyloid-Beta: The Dust-Raising Effect," *J Neuroinflam.* 12:153 (2015).
Makarova, et al., "A DNA Repair System Specific for Thermophilic Archaea and Bacteria Predicted by Genomic Context Analysis," *Nucleic Acids Res.* 30:482-496 (2002).
Moscou, et al., "A Simple Cipher Governs DNA Recognition by Tal Effectors," *Science* 326:1501 (2009).
Neurath, et al., "New Targets for Mucosal Healing and Therapy in Inflammatory Bowel Diseases," *Nature* 7(1):6-19 (2014).
Olovnikov, et al., "Bacterial Argonaute Samples the Transcriptome to Identify Foreign DNA," *Molecular Cell* 51:594-605 (2013)5.
Ordóñez, et al., "A Single-Chain Variable Fragment Intrabody Prevents Intracellular Polymerization of Z α;-Antitrypsin While Allowing Its Antiproteinase Activity," *The FASEB Journal* 29(6):2667-2678 (2016).
Palmer, Alan M.. "New and Emerging Immune-Targeted Drugs for the Treatment of Multiple Sclerosis," *Br J Clin Pharm.* 78(1):33-43 (2013).
Perez, et al., "Establishment of HIV-1 Resistance in CD4$^+$ T Cells by Genome Editing Using Zinc-Finger Nucleases," *Nature Biotechnology* 26(7):808-816 (2008).
Polanski, et al., "A List of Candidate Cancer Biomarkers for Target Proteomics," 2:1-48 (2006).
Rice, et al., "Fresolimumab Treatment Decreases Biomarkers and Improves Clinical Symptoms in Systemic Sclerosis Patents," *J Clin Invest.* 125(7):2795-2807 (2015).
Sasada, et al., "Immune Responses to Epidermal Growth Factor Receptor (EGFR) and Their Application for Cancer Treatment," *Front Pharmacol.* 7:405 Published online Oct. 26, 2016 doi: 10.3389/fphar.2016.00405 eCollection (2016).
Schier, et al., "In Vitro and In Vivo Characterization of a Human Anti-c-erbB-2 Single-Chain Fv Isolated From a Filamentous Phage antibody Library," *Immunotechnology*, 1(1):73-81 (1995).
Schier, et al., "Isolation of High-Affinity Monomeric Human Anti-c-erB-2-Single Chin Fv Using Affinity Driven Selection," *J. Mol. Biol.*, 255(1):28-48 (1996).
Schier, et al., "Isolation of Picomolar Affinity Anti-c-erbB-2 SIngle Chain Fv by Molecular Evolution of the Complementarity Determining Regions in the Center of the Antibody Binding Site," *J. Mol. Biol.*, 263(4):551-567 (1996).
Schornack, et al., "Gene-For-Gene-Mediated Recognition of Nuclear-Targeted AVRBS3-Like Bacterial Effector Proteins," *J. Plant Physiol.* 163(3):256-272 (2006).
Segal, el al., "Custom DNA-Binding Proteins Come of Age: Polydactyl Zinc-Finger Proteins," *Curr. Opin. Biotechnol.* 12:632-637 (2001).
Stevens, et al., "Preclinical Characterization of an Anti-Methamphetamine Monoclonal Antibody for Human Use," *mAbs* 6(2):547-555 (2014).
Stork, et al., "Biodistribution of a Biospecific Single-Chain Diabody and Its Half-Life Extended Derivatives," 284(38):25612-25619 (2009).
Suresh, et al., "New Antibody Approaches to Lymphoma Therapy," *J. Hematology & Oncology* 7:58 Published online Sep. 9, 2014 doi:10.1186/s13045-014-0058-4 (2014).
Susuki, et al., "Therapeutic Antibodies: Their Mechanisms of Action and the Pathological Findings They Induce Tn Toxicity Studies," *J Toxicol Pathol.* 28:133-139 (2015).
Swarts, et al. "DNA-Guided DNA Interference by a Prokaryotic Argonaute" *Nature* 507(7491):258-261 (2014).
Tanida, et al., "Advances in Refractory Ulcerative Colitis Treatment: A New Therapeutic Target, Annexin A2," *World Journal Gastroenterology.* 21(29):8776-8786 (2015).
Turner, et al., "Dysregulated Fibroblast Growth Factor (FGF) Signaling in Neurological and Psychiatric Disorders," *Seminars in Cell & Developmental Biology.* 53:136-143 (2016).
Umov, at al., "Highly Efficient Endogenous Human Gene Correction Using Designed Zinc-Finger Nucleases," *Nature* 435(2):646-651 (2005).
Van den Hoogen, et al.,"Use of Monoclonal Antibodies in Renal Transplantation," *Immunotherapy* 3(7):871-880 (2011).
Vogel, Jörg, "A Bacterial Seek-and-Destroy System for Foreign DNA," *Science* 344(6187):972-973(2014).
Wu, et al., "Therapeutic Antibody Targeting of Individual Notch Receptors," *Nature* 464:1052-1057 (2010).
Yuan, et al., "Crystal Structure of *A. aeolicas* Argonaute, A Site-Specific DNA-Guided Endoribonuclease, Provides Insights Into Risc-Mediated mRNA Cleavage," *Molecular Cell* 19:405-419 (2005).
Cantos, et al., "Identification of "Safe Harbor" Loci in Indica Rice Genome by Harnessing the Property of Zinc-Finger Nucleases to Induce DNA Damage and Repair," Frontiers in Plant Science 5(302):1-8 (2014).
Compte, et al., "Inhibition of Tumor Growth In Vivo by in Situ Secretion of Bispecific Anti-Cea X Anti-CD3 Diabodies From Lentivirally Transduced Human Lymphocytes," Cancer Gene Therapy 14(4):380-388 (2007).
Ismaili, et al., "Production and Characterization of Anti-(Mucin Muci) Single-Domain Antibody in Tobacco (*Nicotiana tabacum* Cultivar Xanthi)," Biotechnology and Applied Biochem. 47(Part 1):11-19(2007).
Sakuma, et al., "Homologous Recombination-Independent Large Gene Cassette Knock-In in Cho Cells Using Talen and MMEJ-Directed Donor Plasmids," International Journal of Molecular Sciences 16(10):23849-23866 (2015).
Zhang, et al., "Glycoengineered Pichia Produced Anti-Her2 Is Comparable to Trastuzumab in Preclinical Study," MABS 3(3):289-298 (2011).

\* cited by examiner

Her2 Binding Assay

Levels Assay

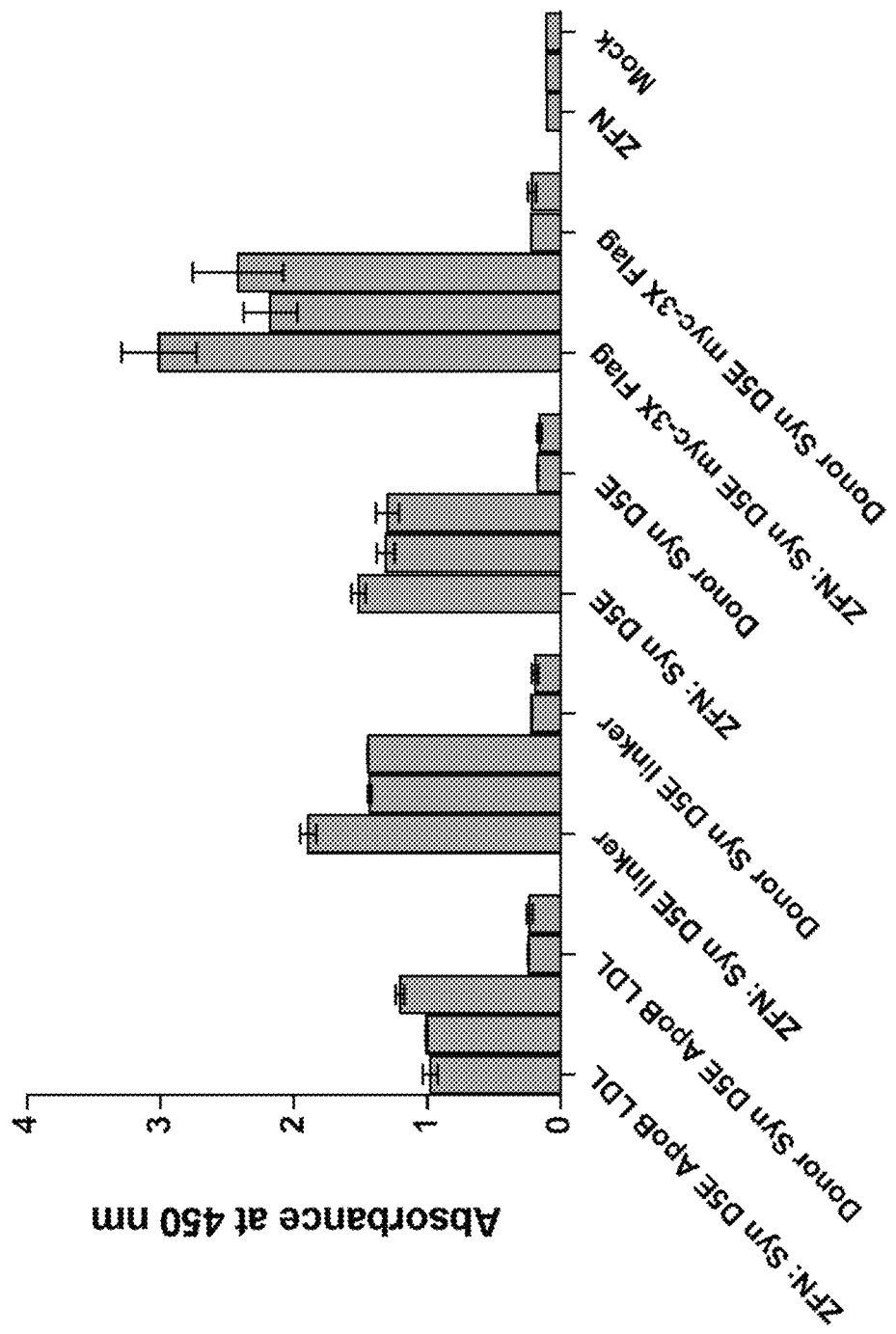

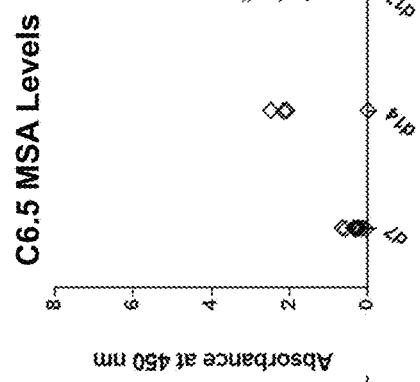
Figure 8C
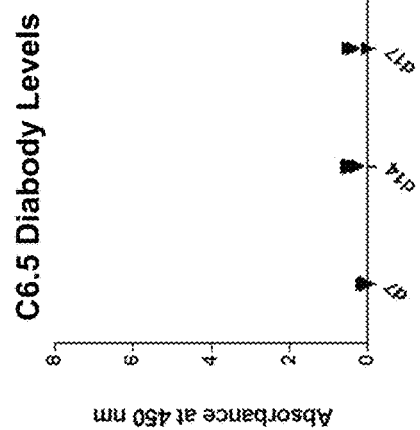
Figure 8B
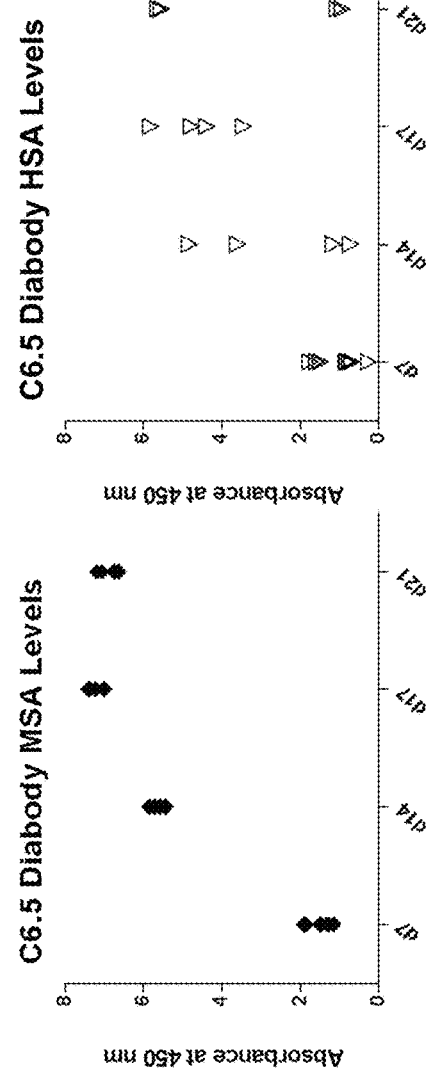
Figure 8E
Figure 8D
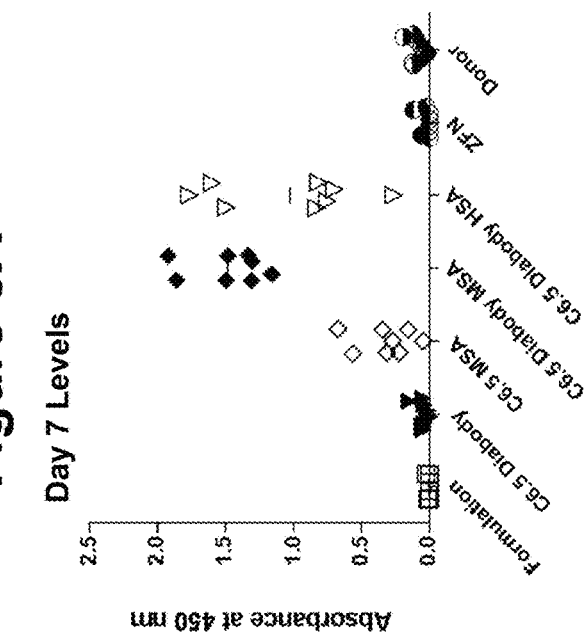
Figure 8A

Figure 11

| Group | ZFN Description | Immune Supp. | ZFN Dose each | Total dose (vg/mouse) | Donor Test article | Time of Donor administration relative to ZFN | Donor dose | ZFN:Donor Ratio | Total dose (vg/mouse) | Total Volume/mouse (L) | N/Time point for serial bleed | | | | | | | Day 28 End of Study |
|---|---|---|---|---|---|---|---|---|---|---|---|---|---|---|---|---|---|---|
| | | | | | | | | | | | Day 7 | Day 14 | Day 17 | Day 21 | Day 24 | Day 27 | |
| 1 | Formulation buffer | 50 mg/kg | Max dose volume | N/A | N/A | N/A | N/A | N/A | N/A | 200 | 6 | 3 | 3 | 3 | 3 | 3 | 6 |
| 2 | AAV2/8 muAlb intron1 ZFN-L AAV2/8 muAlb intron1 ZFN-R | 50 mg/kg | 1.50E+11 1.50E+11 | 3.00E+11 | C6.5 Diabody | same day | 1.20E+12 | 1:1.8 | 1.50E+12 | 200 | 8 | 4 | 4 | 4 | 4 | 4 | 8 |
| 3 | AAV2/8 muAlb intron1 ZFN-L AAV2/8 muAlb intron1 ZFN-R | 50 mg/kg | 1.50E+11 1.50E+11 | 3.00E+11 | C6.5 MSA | same day | 1.20E+12 | 1:1.8 | 1.50E+12 | 200 | 8 | 4 | 4 | 4 | 4 | 4 | 8 |
| 4 | AAV2/8 muAlb intron1 ZFN-L AAV2/8 muAlb intron1 ZFN-R | 50 mg/kg | 1.50E+11 1.50E+11 | 3.00E+11 | C6.5 Diabody MSA | same day | 1.20E+12 | 1:1.8 | 1.50E+12 | 200 | 8 | 4 | 4 | 4 | 4 | 4 | 8 |
| 5 | AAV2/8 muAlb intron1 ZFN-L AAV2/8 muAlb intron1 ZFN-R | 50 mg/kg | 1.50E+11 1.50E+11 | 3.00E+11 | C6.5 Diabody HSA | same day | 1.20E+12 | 1:1.8 | 1.50E+12 | 200 | 8 | 4 | 4 | 4 | 4 | 4 | 8 |
| 6 | AAV2/8 muAlb intron1 ZFN-L AAV2/8 muAlb intron1 ZFN-R | 50 mg/kg | 1.50E+11 1.50E+11 | 3.00E+11 | N/A | N/A | N/A | N/A | 3.00E+11 | 200 | 8 | 4 | 4 | 4 | 4 | 4 | 4 |
| 7 | N/A | 50 mg/kg | N/A | N/A | Donor | N/A | 1.20E+12 | N/A | 1.20E+12 | 200 | 8 | 4 | 4 | 4 | 4 | 4 | 8 |

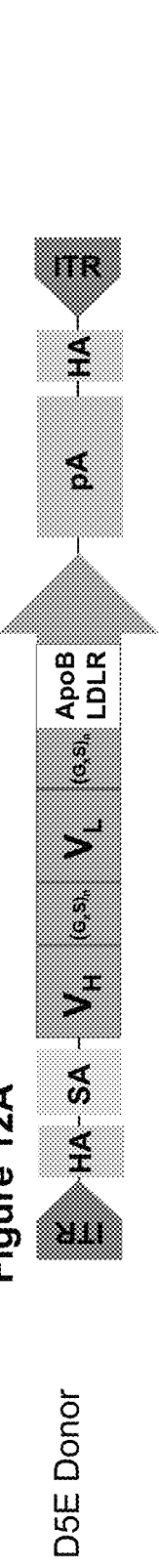
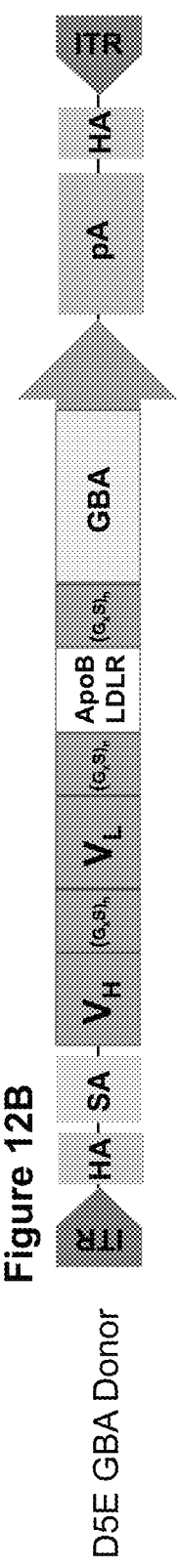
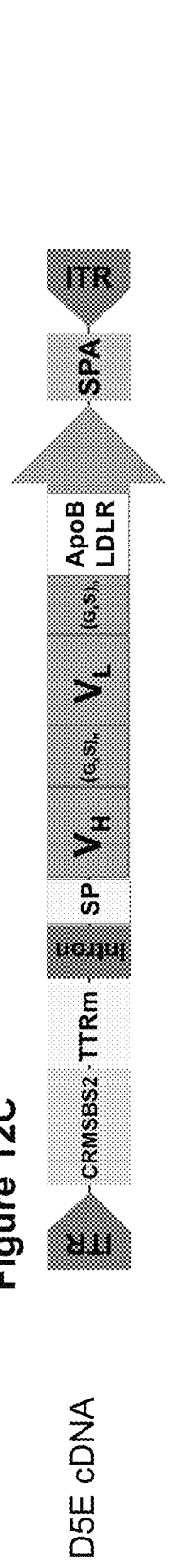
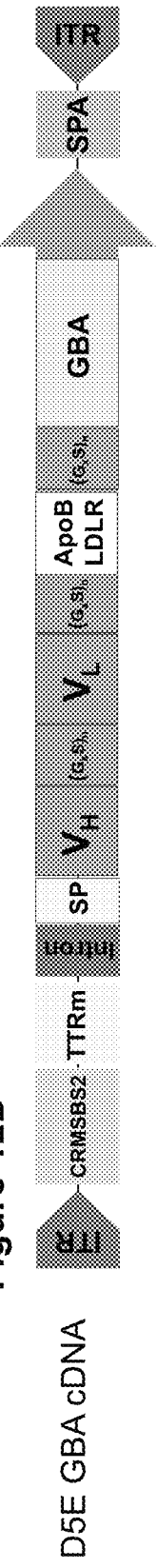
Figure 12A D5E Donor
Figure 12B D5E GBA Donor
Figure 12C D5E cDNA
Figure 12D D5E GBA cDNA

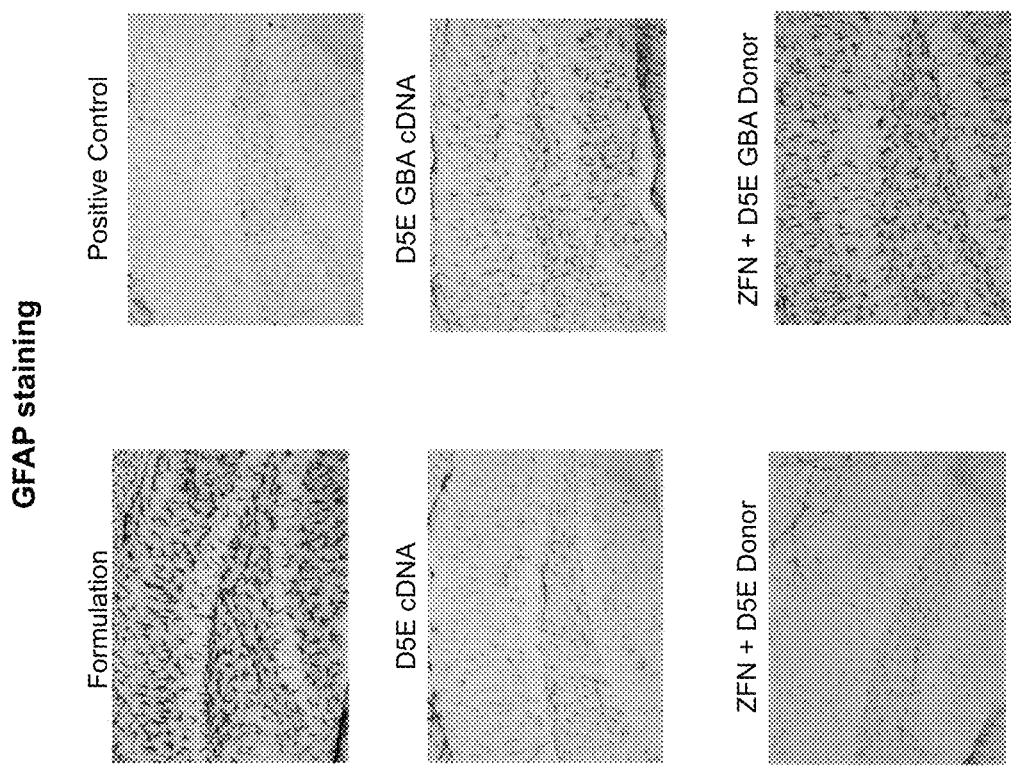

METHODS AND COMPOSITIONS FOR ENGINEERING IMMUNITY

CROSS-REFERENCE TO RELATED APPLICATIONS

The present application claims the benefit of U.S. Provisional Application No. 62/258,864, filed Nov. 23, 2015, and U.S. Provisional Application No. 62/405,521, filed Oct. 7, 2016, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Mar. 20, 2017, is named 83250146SL.txt and is 5,795 bytes in size.

TECHNICAL FIELD

The present disclosure is in the field of genome editing.

BACKGROUND

Gene therapy holds enormous potential for a new era of human therapeutics. These methodologies will allow treatment for conditions that have not been addressable by standard medical practice. Gene therapy can include the many variations of genome editing techniques such as disruption or correction of a gene locus, and insertion of an expressible transgene that can be controlled either by a specific exogenous promoter fused to the transgene, or by the endogenous promoter found at the site of insertion into the genome.

Delivery and insertion of the transgene are examples of hurdles that must be solved for any real implementation of this technology. For example, although a variety of gene delivery methods are potentially available for therapeutic use, all involve substantial tradeoffs between safety, durability and level of expression. Methods that provide the transgene as an episome (e.g. basic adenovirus, AAV and plasmid-based systems) are generally safe and can yield high initial expression levels, however, these methods lack robust episome replication, which may limit the duration of expression in mitotically active tissues. In contrast, delivery methods that result in the random integration of the desired transgene (e.g. integrating lentivirus) provide more durable expression but, due to the untargeted nature of the random insertion, may provoke unregulated growth in the recipient cells, potentially leading to malignancy via activation of oncogenes in the vicinity of the randomly integrated transgene cassette. Moreover, although transgene integration avoids replication-driven loss, it does not prevent eventual silencing of the exogenous promoter fused to the transgene. Over time, such silencing results in reduced transgene expression for the majority of random insertion events. In addition, integration of a transgene rarely occurs in every target cell, which can make it difficult to achieve a high enough expression level of the transgene of interest to achieve the desired therapeutic effect.

In recent years, a new strategy for transgene integration has been developed that uses cleavage with site-specific nucleases (e.g., zinc finger nucleases (ZFNs), TAL-effector domain nucleases (TALENs), CRISPR/Cas system with an engineered crRNA/tracr RNA ('single guide RNA') to guide specific cleavage, etc.) to bias insertion into a chosen genomic locus. See, e.g., U.S. Pat. Nos. 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983; 20130196373; 20140120622; 20150056705; 20150335708; 20160030477 and 20160024474. Further, targeted nucleases are being developed based on the Argonaute system (e.g., from *T. thermophilus*, known as 'TtAgo', see Swarts et al (2014) *Nature* 507(7491): 258-261), which also may have the potential for uses in genome editing and gene therapy. This nuclease-mediated approach to transgene integration offers the prospect of improved transgene expression, increased safety and expressional durability, as compared to classic integration approaches, since it allows exact transgene positioning for a minimal risk of gene silencing or activation of nearby oncogenes.

One approach involves the integration of a transgene into its cognate locus, for example, insertion of a wild type transgene into the endogenous locus to correct a mutant gene. Alternatively, the transgene may be inserted into a non-cognate locus chosen specifically for its beneficial properties. See, e.g., U.S. Patent Publication No. 20120128635 relating to targeted insertion of a factor IX (FIX) transgene. Targeting the cognate locus can be useful if one wishes to replace expression of the endogenous gene with the transgene while still maintaining the expressional control exerted by the endogenous regulatory elements. Specific nucleases can be used that cleave within or near the endogenous locus and the transgene can be integrated at the site of cleavage through homology directed repair (HDR) or by end capture during non-homologous end joining (NHEJ). The integration process is determined by the use or non-use of regions of homology in the transgene donors between the donor and the endogenous locus.

Alternatively, the transgene may be inserted into a specific "safe harbor" location in the genome that may either utilize the promoter found at that safe harbor locus, or allow the expressional regulation of the transgene by an exogenous promoter that is fused to the transgene prior to insertion. Several such "safe harbor" loci have been described, including the AAVS1, CCR5, Rosa26 and albumin in murine cells (see, e.g., U.S. Pat. Nos. 7,951,925; 8,771,985; 8,110,379; 7,951,925; U.S. Publication Nos. 20100218264; 20110265198; 20130137104; 20130122591; 20130177983; 20130177960; 20150056705 and 20150159172). As described above, nucleases specific for the safe harbor genes can be utilized such that the transgene construct is inserted by either HDR- or NHEJ-driven processes.

The field of engineered immunity, via either vaccination or passive immunization, has led to enormous strides in human health. Vaccination of the population alone has resulted in global eradication of small pox and decreased incidence of diphtheria, measles, mumps, pertussis, poliomyelitis, rubella and tetanus. Passive immunization involves the administration of sera or purified antibodies into naïve patients for transient immunity (Deal and Balazs (2015) *Curr Opin in Immunol* 35:113-122), and has been used to rapidly treat exposure to a threat such as rabies or snake venom.

Antibodies are secreted protein products whose binding plasticity has been exploited for development of a diverse range of therapies. Therapeutic antibodies can be used for neutralization of target proteins that directly cause disease (e.g. VEGF in macular degeneration) as well as highly selective killing of cells whose persistence and replication endanger the host (e.g. cancer cells, as well as certain immune cells in autoimmune diseases or virally infected cells). In such applications, therapeutic antibodies take advantage of the body's normal response to its own antibodies to achieve selective killing, neutralization, or clearance of target proteins or cells bearing the antibody's target antigen. Thus, antibody therapy has been widely applied to many human conditions including oncology, rheumatology, transplant, and ocular disease. Examples of antibody therapeutics include Lucentis® (Genentech) for the treatment of macular degeneration, Rituxan® (Biogen Idec) for the treatment of Non-Hodgkin lymphoma, and Herceptin® (Genentech) for the treatment of breast cancer.

Modern therapeutic antibodies come in a variety of configurations. Monoclonal antibodies are typically exact copies of a standard 2 light chain, 2 heavy chain IgG type of molecule. Other examples include Fab, Fab2 and Fab3 antibody fragments, minibodies, diabodies, tribodies, tetrabodies, antibodies based on camel antibodies and novel "antibodies" using other domains such as the transferrin structure as the base of the molecule (Goswami et al (2013) *Antibodies* (2):452). One type of antibody encoded by a single open reading frame is termed a single chain antibody or single chain variable fragment (scFv). These scFv comprise the smallest antigen binding domain of a traditional monoclonal antibody such that the variable regions of the light ($V_L$) and heavy chain ($V_H$) which contain the complementarity determining region (CDR) are joined by a flexible linker (FIG. 1). ScFvs are much smaller than standard monoclonal antibodies and can be engineered with high target binding affinity, and so may more readily penetrate solid tumors and other complex tissues such as the brain. Libraries of scFv exist in yeast and phage, allowing for selection of highly specific antibodies, and the genes encoding these highly specific antibodies can be inserted into viral transduction vectors. Another single chain antibody type is a scFv-Fc antibody, in which the $V_L$ and $V_H$ encoding portions on an antibody are cloned into a single open reading frame. This type of antibody has the advantage of being small enough to have the characteristics of a scFv (tissue penetrance, single polypeptide chain) but also have the Fc portion of the antibody to allow the protein to stimulate typical antibody dependent processes such as complement dependent cytotoxicity (CDC) (see e.g. Hong et al, (2012) *Immune Network* 12(1):33).

However, current antibody therapies have their drawbacks. The cost of production of therapeutic antibodies can be quite high as they often have to be produced in large cultures of mammalian cells, and subjected to extensive purification techniques. Therapeutic treatments often require a substantial amount of antibody (6-12 g of Rituximab per dose for example) Some functional limitations of therapeutic antibodies include inadequate pharmacokinetics and tissue accessibility as well as impaired interactions with the immune system (Chames et al (2009) *Br. J Pharm* 157:220).

Albumin is a protein that is produced in the liver and secreted into the blood. In humans, serum albumin comprises 60% of the protein found in blood, and its function seems to be to regulate blood volume by regulating the colloid osmotic pressure. It also serves as a carrier for molecules with low solubility, for example lipid soluble hormones, bile salts, free fatty acids, calcium and transferrin. In addition, serum albumin carries therapeutics, including warfarin, phenobutazone, clofibrate and phenytoin. In humans, the albumin locus is highly expressed, resulting in the production of approximately 15 g of albumin protein each day. Albumin has no autocrine function, and there does not appear to be any phenotype associated with monoallelic knockouts and only mild phenotypic observations are found for biallelic knockouts (see Watkins et al (1994) *Proc Natl Acad Sci USA* 91:9417).

Albumin has also been used when coupled to therapeutic reagents to increase the serum half-life of the therapeutic. For example, Osborn et al (*J Pharm Exp Thera* (2002) 303(2):540) disclose the pharmacokinetics of a serum albumin-interferon alpha fusion protein and demonstrate that the fusion protein had an approximate 140-fold slower clearance such that the half-life of the fusion was 18-fold longer than for the interferon alpha protein alone. Other examples of therapeutic proteins recently under development that are albumin fusions include Albulin-G™, Cardeva™ and Albugranin™ (Teva Pharmaceutical Industries, fused to Insulin, b-type natriuretic, or GCSF, respectively), Syncria® (GlaxoSmithKline, fused to Glucagon-like peptide-1) and Albuferon α-2B, fused to IFN-alpha (see *Current Opinion in Drug Discovery and Development,* (2009), vol 12, No. 3. p. 288). In these cases, Albulin-G™, Cardeva™ and Syncria® are all fusion proteins where the albumin is found on the N-terminus of the fusion, while Albugranin™ and Albuferon alpha 2G are fusions where the albumin is on the C-terminus of the fusion.

Thus, there remains a need for additional methods and compositions that can be used to express a desired antibody transgene.

SUMMARY

Disclosed herein are methods and compositions for targeted insertion and subsequence expression of an antibody transgene, for example expression of the antibody from a secretory tissue such as liver. In one aspect, the antibody (e.g., ScFv, diabody, intrabody, etc.) is expressed in a cell in vivo following nuclease-mediated targeted integration into a safe harbor gene (e.g., albumin gene) in a liver cell. The nuclease may be a zinc finger nuclease (ZFN), a TALEN, a CRISPR/Cas nuclease system or the like. In certain embodiments, the nuclease comprises a DNA-binding domain (e.g., zinc finger domain, TALE or single guide RNA) that recognizes a target site in a safe harbor gene (e.g., AAVS1, CCR5, Rosa, albumin), for example an albumin-targeted zinc finger protein with the recognition helix domains ordered as shown in Table 1 or an albumin-targeted single guide RNA as shown in Table 3. Thus, disclosed herein is a method of expressing, in a cell (e.g., liver cell, muscle, cell or stem cell such as a hematopoietic stem cell or an induced pluripotent stem cell), an antibody (e.g., a single chain fragment variable (ScFv), an intrabody or a diabody) that binds to a protein selected from the group of a cancer antigen, a cellular receptor, a cytokine, a growth factor, a growth factor receptor, a kinase inhibitor, an integrin, α-synuclein, an amyloid protein, and a complement protein, the method comprising, integrating a transgene encoding the antibody into a safe-harbor locus (e.g., albumin gene) of the cell such that the cell produces the antibody. Expression of the transgene can be driven by an endogenous promoter or an exogenous promoter (e.g., that is part of the transgene). The transgene may be expressed with endogenous safe harbor (e.g., albumin sequences) and/or may include albumin-encoding sequences. The cell of the subject may be modified in vivo (in a live subject) or ex vivo (the transgene is integrated into an isolated cell and isolated cell is administered to a live subject). The transgene may be delivered using a non-viral (e.g., plasmid or mRNA) vector or a viral vector (e.g., AAV, Ad, etc.). Also provided are genetically modified cells produced by the methods as described herein, which cells comprise a transgene encoding an antibody integrated into a safe harbor locus. In any of the methods described herein (ex vivo or in vivo), the antibody is expressed in a cell or tissue (e.g., liver, serum, and/or brain) of a subject and further wherein the antibody treats and/or prevents a cancer, an autoimmune disease, a neurological disorder, pain and/or osteoarthritis. One or more nucleases and one or more antibody-encoding transgenes for use in a method of treating a cancer, an autoimmune disease, a neurological disorder, pain and/or osteoarthritis are also provided, the method comprising administering the one or more nucleases and the one or more transgenes to a subject in need thereof to generate a cell that produces the antibody, wherein the antibody binds to a protein involved the cancer, autoimmune disease, neurological disorder, pain and/or osteoarthritis, wherein the transgene is integrated into an endogenous safe-harbor (e.g., albumin) locus of the cell using a non-naturally occurring nuclease and the cell produces the antibody.

In certain embodiments, the compositions used for targeted integration of an antibody-encoding transgene comprise one or more zinc-finger, TALE and/or CRISPR/Cas nucleases (or polynucleotides encoding one or more components of the nucleases) in combination with a pharmaceutically acceptable excipient. The nucleases (components thereof) and/or transgenes may be delivered to a cell (in vitro or in vivo) in polynucleotide form, as mRNA or in plasmid form. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 20120195936). In still further embodiments, the mRNA may comprise a WPRE element (see U.S. Patent Publication No. 20160326548).

The nuclease (or component thereof) may also be delivered using one or more expression vectors comprising a polynucleotide as described herein. In one embodiment, the expression vector is a viral vector. In one aspect, the viral vector exhibits tissue specific tropism.

In another aspect, described herein is a genetically modified host cell comprising a transgene encoding an antibody (e.g., ScFv, diabody, intrabody, etc.) integrated into a safe harbor gene (e.g., albumin) using a nuclease. The antibody can be bind to any target (antigen), including a protein selected from the group of a cancer antigen, a cellular receptor, a cytokine, a growth factor, a growth factor receptor, a kinase inhibitor, an integrin, α-synuclein, an amyloid protein, and a complement protein for instance to treat and/or prevent a cancer, an autoimmune disease, a neurological disorder, pain and/or osteoarthritis. The host cell may be stably transformed or transiently transfected or a combination thereof with one or more nucleases and transgene(s). The nucleases and transgene(s) (donor(s) may be introduced into a cell in vivo or ex vivo. In one embodiment, the host cell is an embryonic stem cell. Non-limiting examples of suitable cells to which the antibody-encoding transgene is integrated include eukaryotic cells or cell lines such as secretory cells (e.g., liver cells, mucosal cells, salivary gland cells, pituitary cells, etc.), blood cells (e.g., red blood cells, B cells, T cells), stem cells, etc. In any of the embodiments described herein the host cell can comprise a non-human embryo cell, for example, of a mouse, rat, rabbit or other mammal cell embryo. In certain embodiments, the antibody-encoding sequence (e.g., ScFv, diabody, intrabody, etc.) is introduced into an albumin gene at or near a nuclease (e.g., ZFN, TALEN and/or CRISPR/Cas nuclease) target site(s) and/or cleavage site, for example within a nuclease target site (including but not limited to the nuclease target sites as shown in U.S. Pat. Nos. 9,394,545; 9,150,847; U.S. Patent Publication No. 20160060656 and SEQ ID NO:11, 12, 13, 15, 17, 19, 21) or cleavage site, or within 1-50 base pairs (or any value therebetween) of the nuclease and/or cleavage sites.

In another aspect, described herein is a method for introducing a transgene encoding an antibody (e.g., ScFv, diabody, intrabody, etc.) a safe harbor gene (e.g., an albumin gene) in a cell, the method comprising: introducing, into the cell, (i) one or more polynucleotides encoding one or more nucleases (e.g., ZFNs, TALENs and/or CRISPR/Cas systems) that bind to a target site in the safe harbor (e.g., albumin gene) and (ii) the transgene under conditions such that the nuclease(s) is (are) expressed and the transgene is integrated into the safe harbor (e.g., albumin gene)\.

The transgene (donor) sequence may be present in the delivery vector comprising the nuclease, present in a separate vector (e.g., mRNA, Ad, AAV or LV vector) or, alternatively, may be introduced into the cell using a different nucleic acid delivery mechanism. Such insertion of a donor nucleotide sequence into the target locus (e.g., albumin gene, other safe-harbor gene, etc.) can result in the expression of the antibody transgene carried by the donor under control of the target locus's (e.g. albumin) genetic control elements. In some aspects, the transgene is under the control of an exogenous promoter, while in other aspects, the transgene is under the control of the promoter at the insertion site (e.g., the albumin promoter when inserted into the albumin gene). In other aspects, insertion of the antibody transgene, for example into an albumin gene, results in expression of an intact exogenous antibody protein sequence and lacks any endogenous (e.g., albumin) encoded amino acids. In other aspects, the expressed exogenous antibody protein is a fusion protein and comprises amino acids encoded by the antibody transgene and by the safe harbor (e.g., n albumin) gene (e.g., from the endogenous target locus or, alternatively from albumin-encoding sequences on the transgene). In some instances, the albumin sequences will be present on the amino (N)-terminal portion of the exogenous antibody protein, while in others, the albumin sequences will be present on the carboxy (C)-terminal portion of the exogenous antibody protein. In other instances, albumin sequences will be present on both the N- and C-terminal portions of the exogenous antibody protein. The albumin sequences may include full-length wild-type or mutant albumin sequences or, alternatively, may include partial albumin amino acid sequences. In certain embodiments, the albumin sequences (full-length or partial) serve to increase the serum half-life of the antibody expressed by the antibody transgene to which it is fused and/or as a carrier. In some aspects, the antibody transgene is inserted in a safe harbor (e.g., albumin gene) in a T cell or in a B cell. In some embodiments, the antibody transgene is regulated by a T cell or B cell-specific promoter. In preferred embodiments, the antibody transgene is inserted into a safe harbor (e.g., albumin) in a B cell and is regulated by a B cell specific promoter (e.g. CD19 or B29 or immunoglobulin kappa light chain). In other preferred embodiments, the antibody transgene is inserted into a safe harbor in a T cell and is regulated by a T cell specific promoter (e.g. Pmed1, TRBC) (Heusohn et al (2002) *J. Immunol* 168:2857). In some embodiments, the antibody transgene is inserted into a hematopoietic stem cell where the transgene construct comprises the cell-type specific promoter such that the transgene is expressed following stem cell differentiation. In other embodiments, the T and/or B cells are harvested from a donor and the antibody transgene construct is introduced ex vivo, and then the engineered cells are reintroduced back into the donor or into a patient in need thereof. In preferred embodiments, the transgene construct is integrated into the genome of the T and/or B cell using nuclease (ZFN, TALEN, CRISPR/Cas) driven targeted integration.

In another aspect, the invention describes methods and compositions that can be used to express an antibody transgene under the control of a safe harbor gene (e.g., albumin) promoter in vivo (e.g., an endogenous promoter or exogenous promoter that is part of the transgene). In some aspects, the antibody transgene may encode a therapeutic antibody, for example an antibody which when binds to its target (antigen) provides clinical (therapeutic) benefits in a subject with a disorder. In certain embodiments, the antibody recognizes a cancer antigen and may provide for treatment and/or prevention of a cancer. Non-limiting examples of cancer antigens include CD20, CD22, CD19, CD33, CD40, CD52, CCR4, WT-1, HER2, CD137, OX40, EGFR, VEGF, EPCAM, alphafetoprotein (AFP), CEA, CA-125, Muc1, epithelial tumor antigen (ETA), and tyrosinase (for a more extensive list, see Polanski and Anderson (2006) Biomarker Insights 2:1-48). Additionally, antibodies useful for oncology applications include check point inhibitors such as PD1 and CTLA4 (Suresh et al (2014) *J Hematol Oncol* 7:58). Other cancer targets include cancer/testis (CT) antigens, including for example only, MAGE-A-A4, MAGE-C1, SSX2, SSX4, NY-ESO-1, SCP1, CT7. NH-SAR-35, OY-TES-1, SLCO6A1, PASD1, CAGE-1, KK-LC-1 to list just a few of the numerous CT antigens (Cabellero and Chen (2009) *Cancer Sci* 100(11):2014-2021). In other embodiments, the antibody encoded by the integrated transgene recognizes an inflammatory response regulator and is useful for autoimmune therapy. Conditions that may be treated by these antibodies include at least rheumatoid arthritis, inflammatory bowel disease, Crohn's disease, celiac disease, ulcerative colitis, asthma, psoriasis, diabetic retinopathy, Grave's disease, Hashimoto's disease, multiple sclerosis, Lupus, Type I diabetes, glaucoma, neuromyelitis optica, vasculitis and scleroderma. Non-limiting examples of antibody targets useful for treatment of inflammatory conditions include cytokines (IL-2, IL-8, IL-6R, IL-12, IL-23, IL-17, IL-22, IL-26, RANKL), Jak kinase inhibitors, TGF-β, α4β7 integrin, α4β1 integrin, TNFα, CD52, CD25, CD20, annexin A2 and the classical complement pathway including C1q (Tanida et al (2015) *World J Gastro* 21(29):8776-86; Neurath (2014) *Nature* 7(1):6; Rice et al (2015) *J Clin Invest* 125(7):2795; Palmer (2013) *Br J Clin Pharm* 78(1):33-43).

In some embodiments, the antibody is a therapeutic antibody and targets (binds to) a receptor and is useful for the treatment of cancer (Zhu et al (2015) *Lancet* 16 (15) e543-e554). In some embodiments, the therapeutic antibody targets other cellular receptors (e.g. Notch receptors (Wu et al (2010) *Nature* 464:1052-1057), G-protein coupled receptors (Jo et al, (2016) *Exp Mol Med.* 48(2). In other embodiments, the antibody recognizes (binds to) a growth factor receptor and is useful for cancer, neurological and psychiatric disorders (Turner et al (2015) *Semin Cell Dev Biol.* October 8. pii: S1084-9521(15)00188-3. doi: 10.1016/j.semcdb.2015.10.003). In some embodiments, the antibody targets the human epidermal growth factor receptor 2 (HER2) and is useful for the treatment of cancer (Sasada et al (2016) *Front Pharmacol.* 7:405. eCollection 2016). Other non-limiting antibody target examples include α-synuclein for the treatment of Synucleinopathies such as Parkinson's and Multiple Systems Atrophy, amyloid β (Aβ) for Alzheimer's (Liu et al (2015) *J Neuroinflam* 12:153), NGF and TrkA for the treatment of pain and/or Alzheimer's (Hirose et al (2015), *Pain Pract doi:* 10.1111), CGRP for chronic pain and migraine (Bigal et al (2015) *Lancet Neurology* 14(11):1091, and NGF for osteoarthritis (Gow et al (2015) *Arthritis Res Ther doi:* 10.1186).

In other embodiments, the antibody binds to a self-recognition marker and useful for therapy during transplantation. See, e.g., van den Hoogen (2011) *Immunotherapy* 3(7):871-80. Additional therapeutic areas useful for antibody treatment include asthma, psoriasis, cardiac ischemia, viral infection, and hemoglobinuria (see Susuki et al (2015) *J Tox Pathol* 28:133). Other uses of therapeutic antibodies include treatment for drug addiction (Stevens et al (2014) mAbs 6:2: 547; Harris et al (2015) *PLOS ONE* doi:10.1371/journal. pone.0118787).

The methods therefore include in vivo or ex vivo methods of treating and/or preventing any disorder that can be treated and/or prevented by the provision of an antibody. In certain embodiments, the in vivo methods involve administering one or more nucleases targeted to a safe harbor gene (e.g., albumin) and the one or more therapeutic antibody-encoding transgenes to the subject such that the antibody is expressed in the subject. In certain embodiments, the antibody is administered to a first site (e.g., liver) and is also found at one or more secondary sites in the subject (e.g., brain, serum, skeletal muscle, heart, etc.).

In still further embodiments, the antibody produced by the transgene is an engineered intracellular antibody fragment (intrabody). Such intrabodies are useful for inhibiting intracellular processes mediated by proteins. For example, an intrabody produced by the methods and compositions of the invention may target mutant α1-antitrypsin and prevent its polymerization and thus prevent or treat the associated liver damage (see Ordonez et al (2015) FASEB J 29:2667), or may target protease-inhibitor-resistant hepatitis C virus replicons and infectious virus to inhibit resistant hepatitis C replication.

In some aspects, the transgene encoding the antibody comprises a single polynucleotide sequence. In some embodiments, heavy and light chains are encoded in the single polypeptide and are separated by a cleavage sequence (e.g. 2a peptide). In some embodiments, following the cleavage, the exposed polypeptide sequences are available to participate in conjugation reactions. In preferred embodiments, the conjugation reaction involves joining a small molecule to the antibody chain such that upon expression of the antibody, cleavage and conjugation, an antibody-small molecule conjugate is produced and may be secreted.

In other embodiments, the transgene polypeptide encodes a scFv antibody. In still further embodiments, the polypeptide encodes a scFv-Fc antibody. In some embodiments, two transgenes are inserted such that two scFv antibodies are produced. In other embodiments, the antibody comprises two fused scFv where one scFv recognizes an antigen of interest (e.g. cancer antigen) and the other recognizes a T cell antigen, a so-called "BiTE" or bi-specific T cell engager, thus redirecting T-cell driven lysis of a cancer cell (see e.g. Hoffman and Gore (2014) *Front Oncol* 4:63). In other embodiments, the transgene encoding the antibody encodes a single chain diabody These are recombinant molecules composed of the variable heavy and light chain domains of the same or two antibodies connected by three linkers (Stork et al (2009) *J Biol Chem* 284(38):25612-25619). In some instances, the diabody is a bispecific diabody (Kontermann and Brinkmann (2015) *Drug Dis Today* 20(7):838-847).

In some aspects, the antibody encoding donor further comprises a switch to regulate the expression of the antibody. In some embodiments, the switch comprises use of a small-molecule regulatable ribozyme. In some embodiments, the ribozyme acts as a safety switch and is added to the 3' end of the transgene donor. The ribozyme is regulated by a small molecule such that in the presence of the small molecule, the ribozyme is inhibited from self-cleavage (see Kennedy et al (2014) *NAR* 42(19):12306). In other embodiments, the switch comprises the binding of a ligand aptamer to an inducible promoter such that in the presence of the ligand, expression of the promoter is turned on. In still further embodiments, gene switch systems dependent on the binding of a transactivator for induction of gene expression can be used wherein the binding of the transactivator is inhibited by binding to a small molecule such as tetracycline or doxycline (tet OFF), or the binding of the transactivator is dependent on the small molecule to successfully bind to the promoter region (tet-ON).

In some aspects, the invention describes compositions that may be useful for preventing or treating a condition in a subject in need thereof. In some embodiments, the composition comprises a viral vector delivery system comprising targeted nucleases and a specific transgene for integration into a chromosome in vivo. In other embodiments, the transgene comprises a regulatory switch such that expression of the transgene is controllable by the introduction of a regulatory factor into the body. In preferred embodiments, the regulatory factor is a small molecule. In some embodiments, the condition to be treated is a cancer. In other embodiments, the condition is a viral or autoimmune disorder. In further embodiments, the condition is cyclical ("Flaring") such that the symptoms of the condition wax and wane over periods (weeks, months, years) of time in the subject's life. In some embodiments, the transgene is turned on by the activation of the genetic switch during the initial periods of a disease flare. Non-limiting examples of flaring conditions that may be treated or prevented include rheumatoid arthritis, Crohn's disease, inflammatory bowel disease, lupus, asthma, colitis, multiple sclerosis, COPD, and eczema. In some embodiments, the transgene encodes a transmembrane sensor that detects a factor outside of the cell and results in a response by the cell. In some instances, the sensor detects a factor that is generated during a disease flare.

In some embodiments, the methods of the invention may be used in vivo in transgenic animal systems. In some aspects, the transgenic animal may be used in model development where the transgene encodes an antibody that would be used to treat a chronic condition. In some instances, the transgenic animal may be a model system related to a disease (e.g. cancer). Such transgenic models may be used for assessing the therapeutic use of these antibodies for the treatment of prevention of a condition. In other aspects, the transgenic animals may be used for production purposes, for example, to produce antibodies. In certain embodiments, the animal is a small mammal, for example a dog, rabbit or a rodent such as rat, a mouse or a guinea pig. In other embodiments, the animal is a non-human primate. In yet further embodiments, the animal is a farm animal such as a cow, goat or pig. In some aspects, the antibody transgene is integrated into the selected locus (e.g., albumin) into a stem cell (e.g., an embryonic stem cell, an induced pluripotent stem cell, a hepatic stem cell, etc.) or animal embryo obtained by any of the methods described herein, and then the embryo is implanted such that a live animal is born. The animal is then raised to sexual maturity and allowed to produce offspring wherein at least some of the offspring comprise the integrated antibody transgene.

In a still further aspect, provided herein is a method for site specific integration of a nucleic acid sequence encoding an antibody into an endogenous locus (e.g., albumin gene) of a chromosome, for example into the chromosome of an embryo. In certain embodiments, the method comprises: (a) injecting an embryo with (i) at least one DNA vector, wherein the DNA vector comprises an upstream sequence and a downstream sequence flanking the nucleic acid sequence encoding the antibody to be integrated, and (ii) at least one RNA molecule encoding a zinc finger, TALE and/or CRISPR/Cas nuclease that recognizes the site of integration in the target locus (e.g., albumin locus), and (b) culturing the embryo to allow expression of the zinc finger, TALE and/or CRISPR/Cas nuclease, wherein a double stranded break introduced into the site of integration by the nuclease is repaired, via homologous recombination with the DNA vector, so as to integrate the nucleic acid sequence into the chromosome.

Suitable embryos may be derived from several different vertebrate species, including mammalian, bird, reptile, amphibian, and fish species. Generally speaking, a suitable embryo is an embryo that may be collected, injected, and cultured to allow the expression of nuclease. In some embodiments, suitable embryos may include embryos from small mammals (e.g., rodents, rabbits, etc.), companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a *Drosophila* embryo or a mosquito embryo.

In any of the methods or compositions described herein, the cell containing the engineered locus (e.g., albumin locus) can be a stem cell. Specific stem cell types that may be used with the methods and compositions of the invention include embryonic stem cells (ESC), induced pluripotent stem cells (iPSC) and hepatic or liver stem cells. The iPSCs can be derived from patient samples and from normal controls wherein the patient derived iPSC can be mutated to normal gene sequence at the gene of interest, or normal cells can be altered to the known disease allele at the gene of interest. Similarly, the hepatic stem cells can be isolated from a patient. These cells are then engineered to express the transgene of interest, expanded and then reintroduced into the patient.

In some embodiments, the methods and compositions are used to engineer a cell line for production and secretion of antibody. These cell lines are used to produce quantities of antibodies for therapeutic, diagnostic or industrial use. In some embodiments, the cells are mouse cells, while in others, they are hamster cells. In further embodiments, the animal system that the cells are derived from is the best suited for the purpose. In some embodiments, the antibodies are secreted from the cells. In other embodiments, the antibodies are retained within the cell (which may be lysed to isolate the antibodies or administered to a patient in ex vivo therapies).

Also provided is an embryo comprising at least one DNA vector, wherein the DNA vector comprises an upstream sequence and a downstream sequence flanking the nucleic acid sequence encoding an antibody to be integrated, and at least one RNA molecule encoding a nuclease that recognizes the chromosomal site of integration. Organisms derived from any of the embryos as described herein are also provided (e.g., embryos that are allowed to develop to sexual maturity and produce progeny).

In another aspect provided by the methods and compositions of the invention is the use of cells, cell lines and animals (e.g., transgenic animals) in the screening of drug libraries and/or other therapeutic compositions (i.e., antibodies, structural RNAs, etc.) for use in treatment of an animal afflicted with a disorder, for example a disorder which can be treated and/or prevented using an antibody. Such screens can begin at the cellular level with manipulated cell lines or primary cells, and can progress up to the level of treatment of a whole animal (e.g., human).

A kit, comprising the antibody-encoding transgenes and/or nucleases (ZFNs, TALENs and/or CRISPR/Cas systems) is also provided. The kit may comprise nucleic acids encoding the ZFNs, TALENs or CRISPR/Cas system (e.g. RNA molecules genes encoding the nuclease(s) contained in a suitable expression vector), donor transgene molecules, suitable host cell lines, instructions for performing the methods of the invention, and the like.

These and other aspects will be readily apparent to the skilled artisan in light of disclosure as a whole.

BRIEF DESCRIPTION OF THE DRAWINGS

FIG. 3A shows an exemplary single chain fragment variable (ScFv) design for a donor molecule. FIG. 3B shows an exemplary design for a diabody donor. FIG. 3C shows an exemplary design for a ScFv-albumin fusion donor. FIG. 3D shows an exemplary design for a diabody-albumin fusion donor. The antibody donors depicted in FIGS. 3A through 3D lack promoter/enhancer regions. FIG. 3E shows an exemplary ScFv donor design with a C-terminal blood brain barrier targeting motif, in this example residues 3371-3409 of human apolipoprotein B-100 low density lipoprotein was used. "ITR" refers to Inverted Terminal Repeats from an AAV viral vector. "HA" refers to a homology arm, "SA" refers to a splice acceptor sequence. "$V_H$" and "$V_L$" refer to the antibody variable regions from an antibody heavy or light chain, respectively. "$(G_xS)_n$" refers to the linker sequence between the two variable domains. "ApoB LDLR" is the human apolipoprotein B-100 low density lipoprotein (ApoB LDL) residues 3371-3409, and "pA" refers to a polyadenylation signal.

FIG. 5A shows total levels of engineered antibody detected in Hepa1-6 cellular supernatant following administration of albumin-targeted ZFNs and antibody donors to Hepa1-6 cells. In this experiment, Her2 C6.5 Diabody was used as the engineered antibody donor. FIG. 5B is a graph depicting Her2 C6.5 Diabody binding to Her2, demonstrating antibodies produced from the albumin locus were folded properly and bound the intended target. Data shown for ZFN:Donors are of n=3 biological replicates. Error bars represent the standard deviation of technical replicates.

FIG. 6A shows total levels of engineered antibody-albumin fusions detected in Hepa1-6 cellular supernatant following administration of albumin-targeted ZFNs and antibody-albumin donors to Hepa1-6 cells. In this experiment, Her2 C6.5 Diabody-MSA (mouse serum albumin) fusion was used as the antibody donor. FIG. 6B is a graph depicting Her2 C6.5 Diabody-MSA binding to Her2, demonstrating antibodies produced from the albumin locus are folded properly and bind the intended target. Data shown for ZFN:Donors are of n=3 biological replicates. Error bars represent the standard deviation of technical replicates.

FIG. 7 is a graph depicting in vitro production of engineered alpha-synuclein antibodies following targeted integration of the indicated antibody-encoding transgene into the endogenous albumin locus Total levels of engineered antibody detected in Hepa1-6 cellular supernatant following administration of albumin-targeted ZFNs and antibody donors to Hepa1-6 cells. In this example, various versions of alpha-synuclein D5E (Syn D5E) ScFv were used as the engineered antibody donor. Syn D5E ApoB LDL contains a C-terminal human apolipoprotein B-100 low density lipoprotein peptide, LDL peptide, Syn D5E linker, Syn D5E and Syn D5E myc-3x Flag do not contain a C-terminal ApoB LDL peptide. The Syn D5E linker retains the C-terminal linker present in the Syn D5E ApoB LDL donor, while the Syn D5E and Syn D5E myc-3x Flag do not. The Syn D5E 3x Flag construct results in greater levels likely due to the increased binding ability of the 3x Flag in the ELISA Levels Assay. Data shown for ZFN:Donors are of n=3 biological replicates. Error bars represent the standard deviation of technical replicates.

FIGS. 8A through 8E are graphs showing in vivo production of engineered antibodies following targeted integration of the antibody-encoding transgene into the endogenous mouse albumin locus. FIG. 8A is a graph depicting levels of various engineered C6.5 antibodies following administration of albumin-targeted ZFNs and a variety of C6.5 antibody donors to mice. AAV2/8-ZFNs and AAV2/8-Donor were administered as depicted in Table 1 (see Examples). Plasma collection schedule outlined in Table 5 (see Examples). FIGS. 8B (C6.5 diabody transgene), 8C (C6.5 ScFv-MSA donor transgene), 8D (C6.5 diabody-MSA) and 8E (C6.5 diabody-HSA (human serum albumin) transgene) are graphs depicting levels of the various engineered C6.5 antibody donors over time.

FIG. 11 is a table showing all the in vivo dosing groups used in the studies described in Example 3.

FIGS. 12A through 12D are schematics depicting exemplary antibody donor and cDNA constructs. FIG. 12A shows an exemplary single chain fragment variable (ScFv) design with a C-terminal blood brain barrier targeting motif, in this exemplary construct residues 3371-3409 of human apolipoprotein B-100 low density lipoprotein was used. This example represents the alpha-synuclein D5E ScFv. FIG. 12B shows an exemplary ScFv-GBA fusion design. In this exemplary construct, the alpha-synuclein ScFv was fused to GBA. FIG. 12C depicts an exemplary ScFv cDNA, which includes alpha-synuclein ScFv D5E in a cDNA backbone driven by a liver-specific promoter module including an enhancer (CRMSBS2), promoter (TTRm) and intron (SBRIntron 3). The signal peptide is derived from albumin in this example. The polyadenylation signal is a synthetic polyadenylation signal. FIG. 12D shows an exemplary ScFv GBA cDNA, in which the alpha-synuclein ScFv D5E is in a cDNA backbone driven by a liver-specific promoter module including an enhancer (CRMSBS2), promoter (TTRm) and intron (SBRIntron 3). The ScFv is fused to GBA. The signal peptide is derived from albumin in this example. The polyadenylation signal is a synthetic polyadenylation signal. CRM refer to cis-regulatory module. SBS1/2 refers to Sangamo Biosciences 1 and 2. TTRm refers to transthyretin minimal promoter. SBS refers to Sangamo Biosciences. SP refers to signal peptide. ITR refers to inverted terminal repeat. SPA refers to synthetic poly adenylation sequence. GBA refers to glucocerebrosidase. The liver specific constructs used are described in detail in U.S. Publication No. 20170119906.

FIG. 13A is a graph depicting circulating plasma levels the engineered alpha-synuclein D5E antibody following administration of albumin-targeted ZFNs and the alpha-synuclein D5E antibody donor to mice. AAV2/8-ZFNs and AAV2/8-Donor were administered as depicted in Table 6. Plasma collection schedule outlined in Table 7. FIG. 13B is a graph depicting circulating plasma levels the engineered alpha-synuclein D5E GBA antibody following administration of albumin-targeted ZFNs and the alpha-synuclein D5E antibody donor to mice. GBA refers to glucocerebrosidase. AAV2/8-ZFNs and AAV2/8-Donor were administered as depicted in Table 6. Plasma collection schedule outlined in Table 7.

FIG. 14A shows the % Indels for the mouse study at 28 days and post-test article administration and FIG. 14B shows the % Indels at 56 days post-test article administration. Cohorts 1 (Day 28) and Cohort 2 (Day 56) are outlined in Table 8.

FIG. 15 shows representative immunohistochemistry images of the cortex from alpha-synuclein transgenic line 61 mice receiving the indicated treatments (donors and/or ZFNs). Sections were stained with GFAP (Glial fibrillary acidic protein) followed by HRP conjugated secondary antibodies and visualized with DAB. A reduction in the astrogliosis disease endpoint, GFAP is shown in mice receiving donor and/or ZFN treatment as described herein.

FIG. 16A shows levels of D5E (+/−GBA) antibody mRNA expressed in liver were measured by quantitative RT-PCR using a primer/probe contained within the heavy chain of the antibody. FIG. 16B levels of the endogenous albumin-D5E (+/−GBA) fusion mRNA expressed in liver were measured by quantitative RT-PCR. The 5' primer and probe is located within the endogenous mouse albumin locus, and the 3' primer within the engineered D5E (+/−GBA) antibody donor heavy chain. The D5E (+/−GBA) antibody cDNA contains the albumin signal peptide, thus the primer probe detects both the hybrid albumin-D5E (+/−GBA) mRNA from an integrated antibody, but also the D5E (+/−GBA) cDNA mRNA.

FIG. 17A is a graph depicting the comparison between the corrected optical density for alpha-synuclein in the cortex neuropil and the levels of antibody in cortex (denoted by myc). The formulation group was included in the analyses (if removed the significance increased) p value=0.0448. FIG. 17B is a graph depicting the comparison between the corrected optical density for alpha-synuclein in the striatum and the levels of antibody in striatum (denoted by myc). The formulation group was included in the analyses (if removed the significance increased) p value=0.0399.

FIG. 18A shows analysis of alpha-synuclein positive neurons in the cortex. There was a reduction in the total number of alpha-synuclein positive neurons in the cortex for both the cDNA antibody treated groups however this was only statistically significant in the D5E GBA antibody cDNA group. Statistical difference (*) was determined with one-way ANOVA with post-hoc analysis p<0.05. FIG. 18B shows results of quantitative RT-PCR analysis of total CNS examining the astrogliosis marker GFAP. There was a reduction in GFAP for both cDNA groups however was only statistically significant in the D5E GBA antibody cDNA group. p value=0.021.

DETAILED DESCRIPTION

Figure 1:
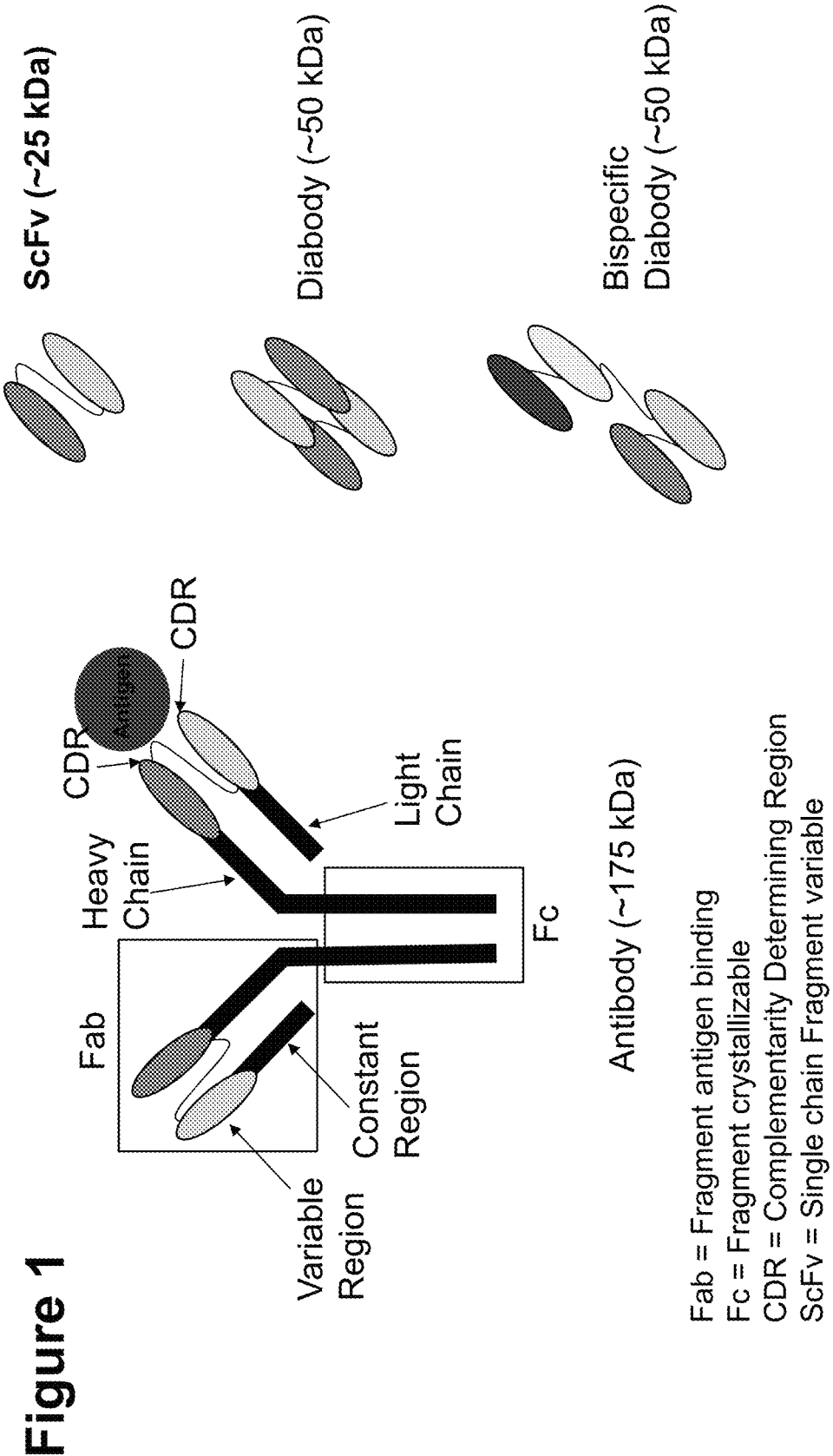
FIG. 1 depicts a simplified overview of antibody architecture. Meanings of the abbreviations are shown at the bottom of the figure.

Disclosed herein are compositions and methods for expressing an antibody at an endogenous locus, for example at safe harbor gene such as an albumin gene. The transgenic antibody can be expressed at the albumin locus in the liver for secretion into the blood stream or may be maintained in the cell as an intrabody. Regulation of the expression of the antibody can be regulated by an expression switch. The antibody can encode any antibody, including those providing therapeutic benefit.

Thus, the methods and compositions of the invention can be used to express therapeutically beneficial antibody proteins (from a transgene) from highly expressed loci in secretory tissues. For example, the antibody transgene can encode as antibody useful for the treatment of or prevention of disorders of the blood, for example, and a variety of other monogenic diseases. In some embodiments, the antibody transgene can be inserted into the endogenous albumin locus such that expression of the antibody transgene is controlled by the albumin expressional control elements, resulting in liver-specific expression of the transgene encoded antibody at high concentrations. Antibodies that may be expressed may be targeted to certain antigens useful in the treatment of oncology, rheumatology, transplant, and ocular disease.

In addition, any transgene can be introduced into patient derived cells, e.g. patient derived induced pluripotent stem cells (iPSCs) or other types of stem cells (embryonic, hematopoietic, neural, or mesenchymal as a non-limiting set) for use in eventual implantation into secretory tissues. The transgene can be introduced into any region of interest in these cells, including, but not limited to, into an albumin gene or a safe harbor gene. These altered stem cells can be differentiated for example, into hepatocytes and implanted into the liver. Alternately, the transgene can be directed to the secretory tissue as desired through the use of viral or other delivery systems that target specific tissues. For example, use of the liver-trophic adenovirus associated virus (AAV) vector AAV8 as a delivery vehicle can result in the integration of the transgene at the desired locus when specific nucleases are co-delivered with the transgene.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Patent Publication No. 20110301073, incorporated by reference herein in its entirety.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878;

WO 01/60970; WO 01/88197; WO 02/099084 and U.S. Publication No. 20110301073.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any value therebetween) sequence identity to the genomic sequence that is replaced. In other embodiments, the homology between the donor and genomic sequence is higher than 99%, for example if only 1 nucleotide differs as between donor and genomic sequences of over 101 contiguous base pairs. In certain cases, a non-homologous portion of the donor sequence can contain sequences not present in the region of interest, such that new sequences are introduced into the region of interest. In these instances, the non-homologous sequence is generally flanked by sequences of 10-1,000 base pairs (or any integral value there between) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 8,623,618; 8,409,861; 8,034,598; 7,914,796; and 7,888,121, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, deubiquitinases topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a protein DNA-binding domain and a cleavage domain), fusions between a polynucleotide DNA-binding domain (e.g., sgRNA) operatively associated with a cleavage domain, and fusion nucleic acids (for example, a nucleic acid encoding the fusion protein).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALEN as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Secretory tissues" are those tissues that secrete products. Examples of secretory tissues that are localized to the gastrointestinal tract include the cells that line the gut, the pancreas, and the gallbladder. Other secretory tissues include the liver, B cells, tissues associated with the eye and mucous membranes such as salivary glands, mammary glands, the prostate gland, the pituitary gland and other members of the endocrine system. Additionally, secretory tissues include individual cells of a tissue type which are capable of secretion.

The term "antibody" refers to a specific protein capable of binding another molecule (e.g., antigen) or portion thereof (in accordance with this invention, capable of binding to protein). The term includes, but is not limited to, polyclonal antibodies, monoclonal antibodies, antibody fragments, single chain antibodies (e.g., ScFvs, ScFv-Fcs, etc.), diabodies, intrabodies and the like.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

A "switch" or "gene switch" refers to any system used to regulate expression of a transgene. Some gene switches can be regulated by a small molecule to either turn on or off. One of the most well-known examples of a gene switch are the tetracycline-dependent regulatable gene expression systems known as tet-ON and tet-OFF. In these systems, regulation of expression of the transgene is controlled by the interaction of two elements: the tetracycline-response element (TRE), inserted upstream of the transgene of interest, and the tetracycline repressor protein (TetR). The TetR is fused to a viral transactivator VP16, converting tetR to an activator tTA. The tTA is responsive to a small molecule inducer, tetracycline or doxycycline, such that in presence of the inducer, the tTA-inducer is able to bind to the TRE and activate expression (tet-ON), or such that the tTA-inducer is unable to bind to the TRE (tet-OFF). Use of such a switch system in vivo allows expression of the transgene to be controlled by the presence of the small molecule (see Goverdhana et al (2005) *Mol Ther* 12(2): 189-211). Another switch system utilizes a small molecule binding aptamer that changes conformation when bound to its ligand, and works with the tet-OFF system. Aptamers that are designed to act intracellularly are also termed intramers, and in some embodiments, use of an intramer system can regulate a transgene in vivo. The intramer is a nucleic acid sequence that, in the presence of its ligand (e.g. theophylline), disrupts the interaction of the tTA and the TRE, and thus inhibits the expression of the transgene (Auslander et al (2011) *NAR* 39(22): e155).

Nucleases

Described herein are compositions, particularly nucleases, which are useful targeting a gene for the insertion of a transgene, for example, nucleases that are specific for albumin. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains, CRISPR/Cas nuclease systems and/or Ttago systems).

A. DNA-Binding Domains

Any DNA-binding domain can be used in the methods disclosed herein. In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family (SEQ ID NO: 27), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Duj on et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVD) at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN). See, e.g., U.S. Pat. No. 8,586,526; Christian et al ((2010) <*Genetics epub* 10.1534/genetics.110.120717). In certain embodiments, TALE domain comprises an N-cap and/or C-cap as described in U.S. Pat. No. 8,586,526. In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs).

In certain embodiments, the DNA-binding domain is part of a CRISPR/Cas nuclease system, for example a single guide RNA that binds to a DNA target. See, e.g., U.S. Pat. No. 8,697,359 and U.S. Patent Publication No. 20150056705. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoSComput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to effect a panoply of outcomes including gene knock-out, targeted gene addition, gene correction, targeted gene deletion using techniques standard in the art for exploitation of DNA breaks.

B. Cleavage Domains

The nucleases described herein (e.g., ZFNs, TALENs, CRISPR/Cas nuclease) also comprise a nuclease (cleavage domain, cleavage half-domain). The nuclease(s) can induce a double-stranded (DSB) or single-stranded break (nick) in the target DNA. In some embodiments, two nickases are used to create a DSB by introducing two nicks. In some cases, the nickase is a ZFN, while in others, the nickase is a TALEN or a CRISPR/Cas nickase.

The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof).

In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites, but may lie 1 or more kilobases away from the cleavage site, including between 1-50 base pairs (or any value therebetween), 1-100 base pairs (or any value therebetween), 100-500 base pairs (or any value therebetween), 500 to 1000 base pairs (or any value therebetween) or even more than 1 kb from the cleavage site.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease, or a DNA binding domain from a CRISPR/Cas system and a cleavage domain from a difference nuclease. Heterologous cleavage domains can be obtained from any endonuclease or exonuclease. Exemplary endonucleases from which a cleavage domain can be derived include, but are not limited to, restriction endonucleases and homing endonucleases. Additional enzymes which cleave DNA are known (e.g., S1 Nuclease; mung bean nuclease; pancreatic DNase I; micrococcal nuclease; yeast HO endonuclease. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,623,618; 8,409,861; 8,034,598; 7,914,796; and 7,888,121, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Pat. No. 7,888,121, the disclosure of which is incorporated by reference in its entirety for all purposes.

Cleavage domains with more than one mutation may be used, for example mutations at positions 490 (E→K) and 538 (I→K) in one cleavage half-domain to produce an engineered cleavage half-domain designated "E490K: 1538K" and by mutating positions 486 (Q→E) and 499 (I→L) in another cleavage half-domain to produce an engineered cleavage half-domain designated "Q486E:I499L;" mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively); engineered cleavage half-domain comprising mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively); and/or engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598 and 8,623,618, the disclosures of which are incorporated by reference in its entirety for all purposes. In other embodiments, the engineered cleavage half domain comprises the "Sharkey" and/or "Sharkey" mutations (see Guo et al, (2010) *J. Mol. Biol.* 400(1):96-107).

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek (2012) *Science* 337(6096): 816-21 and Cong (20130 *Science* 339(6121):819-23).

Target Sites

As described in detail above, DNA domains can be engineered to bind to any sequence of choice in a locus, for example an albumin or other safe-harbor gene. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534, 261, incorporated by reference herein in their entireties. Rational design of TAL-effector domains can also be performed. See, e.g., U.S. Patent Publication No. 20110301073.

Exemplary selection methods applicable to DNA-binding domains, including phage display and two-hybrid systems, are disclosed in U.S. Pat. Nos. 5,789,538; 5,925,523; 6,007, 988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-finger zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Publication No. 20110301073.

Donors

As noted above, insertion of an exogenous sequence (also called a "donor sequence" or "donor"), for example for correction of a mutant gene or for increased expression of a wild-type gene or, preferably, integration of one or more transgenes encoding one or more exogenous antibodies, for treatment and/or prevention of a disorder. Non-limiting examples of antibodies that can be used in the methods and composition of the disclosure include: antibodies that recognize cancer antigens; antibodies that recognize proteins involved in autoimmune conditions such as rheumatoid arthritis, inflammatory bowel disease, Crohn's disease, celiac disease, ulcerative colitis, asthma, psoriasis, diabetic retinopathy, Grave's disease, Hashimoto's disease, multiple sclerosis, Lupus, Type I diabetes, glaucoma, neuromyelitis optica, vasculitis and scleroderma; antibodies that bind to growth factors and/or antibodies that bind to proteins involved in neurological and psychiatric disorders (e.g., α-synuclein for the treatment of Synucleinopathies such as Parkinson's and Multiple Systems Atrophy, as well as Alzheimer's), pain (including chronic pain and migraine) and/or osteoarthritis.

Thus, non-limiting examples of antibody targets (to which the antibodies expressed from the transgene bind) useful for treating these conditions include antibodies that bind to: one or more cancer antigens (e.g., CD20, CD22, CD19, CD33, CD40, CD52, CCR4, WT-1, HER2, CD137, OX40, EGFR, VEGF, EPCAM, alphafetoprotein (AFP), CEA, CA-125, Muc1, epithelial tumor antigen (ETA), tyrosinase (for a more extensive list, see Polanski and Anderson (2006) *Biomarker Insights* 2:1-48); PD1 and CTLA4 (Suresh et al (2014) *J Hematol Oncol* 7:58), cancer/testis (CT) antigens (e.g., MAGE-A-A4, MAGE-C1, SSX2, SSX4, NY-ESO-1, SCP1, CT7. NH-SAR-35, OY-TES-1, SLCO6A1, PASD1, CAGE-1, KK-LC-1); cytokines (IL-2, IL-8, IL-6R, IL-12, IL-23, IL-17, IL-22, IL-26, RANKL), Jak kinase inhibitors, TGF-β, α4β7 integrin, α4β1 integrin, TNFα, CD52, CD25, CD20, annexin A2, proteins involved in the classical complement pathway including C1q, growth factors, and/or proteins found in the brain and other tissues such as α-synuclein, amyloid β (Aβ), NGF, TrkA, CGRP and/or NGF. See, e.g., Tanida et al (2015) *World J Gastro* 21(29):8776-86; Neurath (2014) *Nature* 7(1):6; Rice et al (2015) *J Clin Invest* 125(7):2795; Palmer (2013) *Br J Clin Pharm* 78(1): 33-43); Turner et al (2015) *Semin Cell Dev Biol.* October 8. pii: S1084-9521(15)00188-3. doi: 10.1016/j.semcdb.2015.10.003); Liu et al (2015) *J Neuroinflam* 12:153); Hirose et al (2015), *Pain Pract doi:*10.1111; Bigal et al (2015) *Lancet Neurology* 14(11):1091, Gow et al (2015) *Arthritis Res Ther doi:*10.1186); Cabellero and Chen (2009) *Cancer Sci* 100(11):2014-2021. The antibody target may or may not be aberrantly expressed in a subject with a condition to be treated and/or prevented, for example cancer antigens and proteins as such α-synuclein may be aberrantly expressed in subjects with cancer or synucleopathies.

It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See, e.g., U.S. Pat. Nos. 8,703,489 and 9,255,259. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272: 886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLY)).

The donor is generally inserted so that its expression is driven by the endogenous promoter at the integration site, namely the promoter that drives expression of the albumin gene. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an albumin locus such that some or none of the endogenous albumin sequences are expressed, for example as a fusion with the transgene.

In other embodiments, the transgene (e.g., with or without albumin encoding sequences) is integrated into any endogenous locus, for example a safe-harbor locus. See, e.g., US patent publications 20080299580; 20080159996 and 201000218264.

When albumin sequences (endogenous or part of the transgene) are expressed with the transgene, the albumin sequences may be full-length sequences (wild-type or mutant) or partial sequences. Preferably the albumin sequences are functional. Non-limiting examples of the function of these full length or partial albumin sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger or TALEN protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adeno-viral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors is described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV 8.2, AAV9, AAV rh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) Nature Genetics 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by a plasmid, while the one or more nucleases can be carried by an AAV vector. Furthermore, the different vectors can be administered by the same or different routes (intramuscular injection, directly to the liver (e.g., tail vein injection), other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions of the invention can be used in any circumstance wherein it is desired to supply a transgene encoding an antibody such that the antibody is secreted from the targeted cell connected to a transmembrane domain and/or expressed as an intrabody within the target cell. Thus, this technology is of use in a condition where a patient has a condition that can be prevented or treated with a therapeutic antibody. Particularly useful with this invention is the expression of antibodies against cancer antigens, to help target the patient's immune system to cancer cells, and in immune disorders, where antibody therapy is used to dampen immune modulators. Preferred embodiments include use of a small-molecule controlled expression switch to regulate the expression of the antibody transgene. This type of construct may be utilized in the case of diseases that are characterized by periodic flare-ups, in which turning on the expression of the antibody could help dampen the severity of the flare-up and the duration. In other preferred embodiments, the antibodies comprise peptides that allow for the antibody to cross the blood brain barrier. These antibodies can be useful for treatment of brain disorders such as tauopathies (e.g. Alzheimer's Disease), Parkinson's disease, Multiple Systems Atrophy or symptoms associated with lysosomal storage disease.

The following Examples relate to exemplary embodiments of the present disclosure in which the nuclease comprises a zinc finger nuclease (ZFN) or CRISPR/Cas system. It will be appreciated that this is for purposes of exemplification only and that other nucleases can be used, for instance with TALENs, homing endonucleases (meganucleases) with engineered DNA-binding domains and/or fusions of naturally occurring of engineered homing endonucleases (meganucleases) DNA-binding domains and heterologous cleavage domains.

EXAMPLES

Example 1

Design, Construction and Characterization of Engineered Nucleases Targeted to the Albumin Gene Zinc finger proteins were designed to target cleavage sites within intron 1 of the mouse albumin gene (see U.S. Publication Nos. 20130177983 and 20160060656, also shown below in Table 1). Corresponding expression constructs were assembled and incorporated into plasmids, AAV or adenoviral vectors essentially as described in Urnov et al. (2005) *Nature* 435(7042):646-651, Perez et al (2008) *Nature Biotechnology* 26(7):808-816, and as described in U.S. Pat. No. 6,534,261. Table 1 shows the recognition helices within the DNA binding domain of exemplary mouse albumin specific ZFPs while Table 2 shows the target sites for these ZFPs. Nucleotides in the target site that are contacted by the ZFP recognition helices are indicated in uppercase letters; non-contacted nucleotides indicated in lowercase.

Guide RNAs for the *S. pyogenes* CRISPR/Cas9 system were also constructed to target intron 1 in the human albumin gene. See, also, U.S. Publication No. 201500566705 for additional albumin-targeted guide RNAs. The target sequences in the albumin gene are indicated as well as the guide RNA sequences in Table 3 below. It will be apparent that other nucleases (e.g., ZFNs, TALENs, etc.) can also be designed to the target sites shown in Table 3.

TABLE 1

Mouse Albumin Designs

| SBS # | F1 | F2 | F3 | F4 | F5 |
|---|---|---|---|---|---|
| 31523 | RSDNLSE (SEQ ID NO: 1) | QSGNLAR (SEQ ID NO: 2) | DRSNLSR (SEQ ID NO: 3) | WRSSLRA (SEQ ID NO: 4) | DSSDRKK (SEQ ID NO: 5) |
| 48641 | TSGSLTR (SEQ ID NO: 6) | RSDALST (SEQ ID NO: 7) | QSATRTK (SEQ ID NO: 8) | LRHHLTR (SEQ ID NO: 9) | QAGQRRV (SEQ ID NO: 10) |

TABLE 2

Target Sites of mouse albumin-specific zinc fingers

| SBS # | Target site |
|---|---|
| 31523 | ttTCCTGTAACGATCGGgaactggcatc (SEQ ID NO: 11) |
| 48641 | ctGAAGGTgGCAATGGTTcctctctgct (SEQ ID NO: 12) |

TABLE 3

Guide RNAs for human albumin

| Name | Location | Strand | Target | gRNA |
|---|---|---|---|---|
| Alb-f1384 | 1384 | F | TAATTTTCTTTTGCGCACTAAGG (SEQ ID NO: 13) | GTAATTTTCTTTTGCGCACTA (SEQ ID NO: 14) |
| Alb-f1428 | 1428 | F | TGACTGAAACTTCACAGAATAGG (SEQ ID NO: 15) | GTGACTGAAACTTCACAGAAT (SEQ ID NO: 16) |
| Alb-f429 | 1429 | F | GACTGAAACTTCACAGAATAGGG (SEQ ID NO: 17) | GACTGAAACTTCACAGAATA (SEQ ID NO: 18) |
| Alb-r1462 | 1462 | R | TAGTGCAATGGATAGGTCTTTGG (SEQ ID NO: 19) | GTAGTGCAATGGATAGGTCTT (SEQ ID NO: 20) |
| Alb-r1469 | 1469 | R | TAAAGCATAGTGCAATGGATAGG (SEQ ID NO: 21) | GTAAAGCATAGTGCAATGGAT (SEQ ID NO: 22) |
| Alb-r1500 | 1500 | R | GATCAACAGCACAGGTTTTGTGG (SEQ ID NO: 23) | GATCAACAGCACAGGTTTTTG (SEQ ID NO: 24) |

Example 2

Activity of Albumin-Specific Nucleases

The ZFN pair in Table 1 was tested for the ability to cleave endogenous target sequences in mouse cells and was shown to be active (U.S. Publication No. 20160060656).

The human albumin-specific CRISPR/Cas9 systems were tested in human K562 cells. The activity of the CRISPR/Cas9 systems were measured by MiSeq analysis. Cleavage of the endogenous albumin DNA sequence by Cas9 was assayed by high-throughput sequencing (Miseq, Illumina), where the results are shown below in Table 4. Results are expressed as the 'percent indels,' where 'indels' means small insertions and/or deletions found as a result of the error prone NHEJ repair process at the site of a nuclease-induced double strand cleavage.

In these experiments, Cas9 was supplied on a pVAX plasmid, and the sgRNA was supplied on a plasmid under the control of the U6 promoter. The plasmids were mixed at either 100 ng of each or 400 ng of each and were mixed with 2e5 cells per run. The cells were transfected using the Amaxa system. Briefly, an Amaxa transfection kit was used and the nucleic acid transfected using a standard Amaxa shuttle protocol. Following transfection, the cells were let to rest for 10 minutes at room temperature and then resuspended in prewarmed RPMI. The cells were then grown in standard conditions at 37° C. Genomic DNA was isolated 7 days after transfection and subject to MiSeq analysis, and the results are shown below in Table 4.

As can be seen by the data, the activity of the different guide RNAs all induced cleavage at the targeted site.

TABLE 4

Activity of human albumin-specific CRISPR/Cas9 systems

| Name | % Indels, Average (100 ng each) | % Indels, Average (400 ng each) |
|---|---|---|
| Alb-f1384 | 76.2 | 78.5 |
| Alb-f1428 | 3.2 | 13.5 |
| Alb-f1429 | 3.0 | 12.2 |
| Alb-r1462 | 2.2 | 8.6 |
| Alb-r1469 | 8.3 | 20.1 |
| Alb-r1500 | 0.6 | 1.4 |

Example 3

Insertion of Recombinant scFv into the Mouse Albumin Locus

Figure 2:
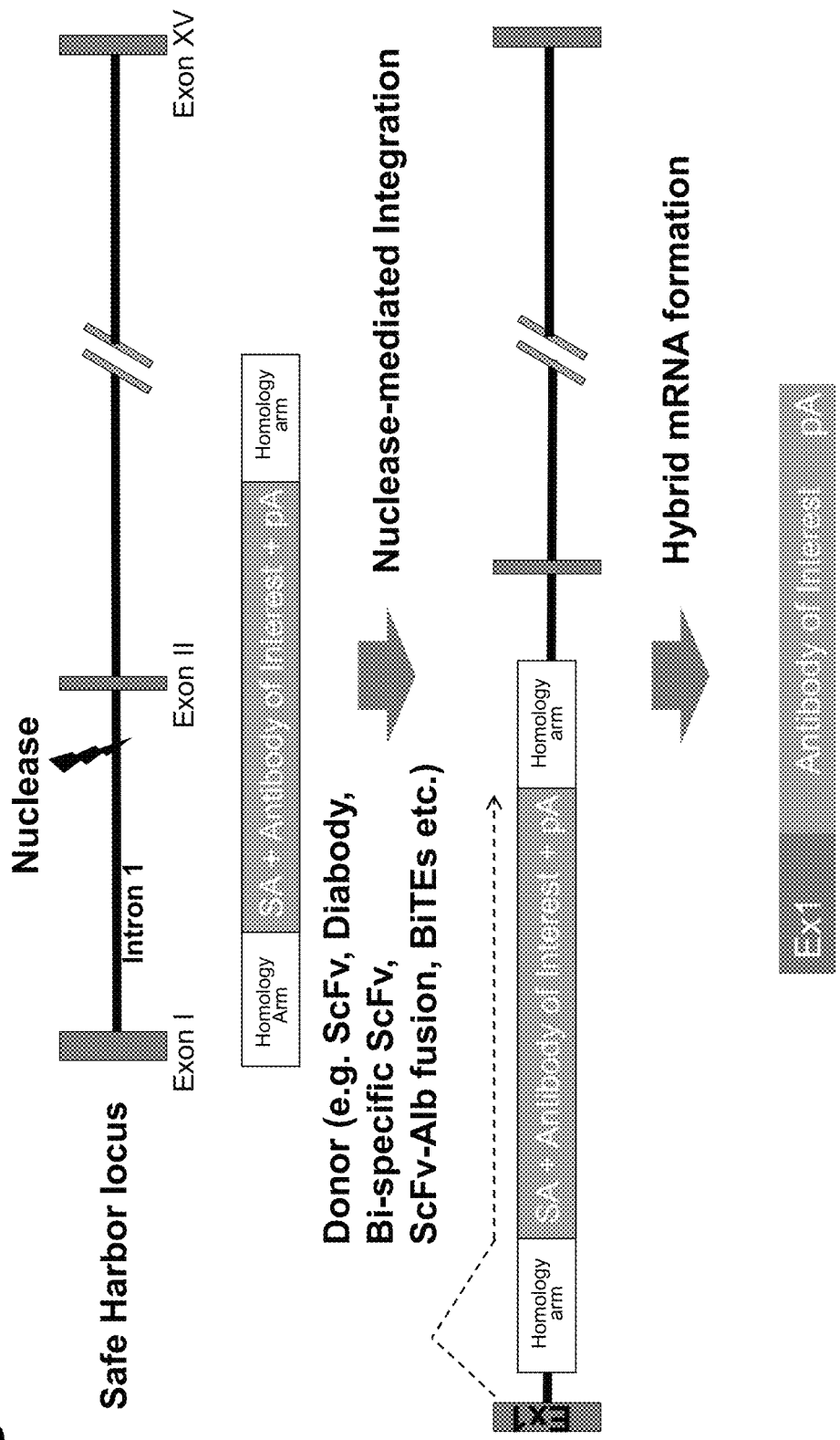
FIG. 2 Is a schematic depicting engineered nuclease-mediated insertion of an engineered antibody at the endogenous safe harbor locus. "SA" refers to a splice acceptor site; "pA" refers to a polyadenylation signal; and "Ex1" refers to exon 1 of the endogenous safe harbor (e.g., albumin) locus. "ScFv" refers to single chain fragment variable and "ScFv-Alb" refers to a chimeric protein comprising ScFv sequences as well as albumin sequences. "BiTE" refers to bi-specific T-cell engager.
Figure 3A:
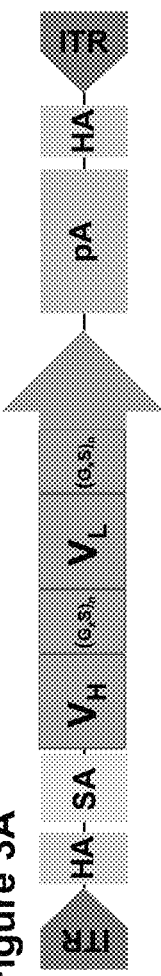
FIGS. 3A through 3E are a series of schematics depicting exemplary antibody donor and nuclease designs.
Figure 3B:
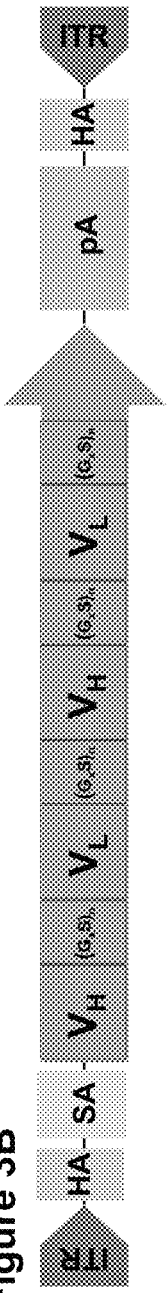
Figure 3C:
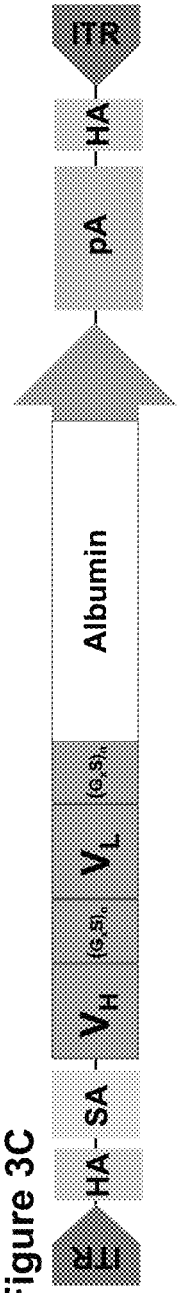
Figure 3D:
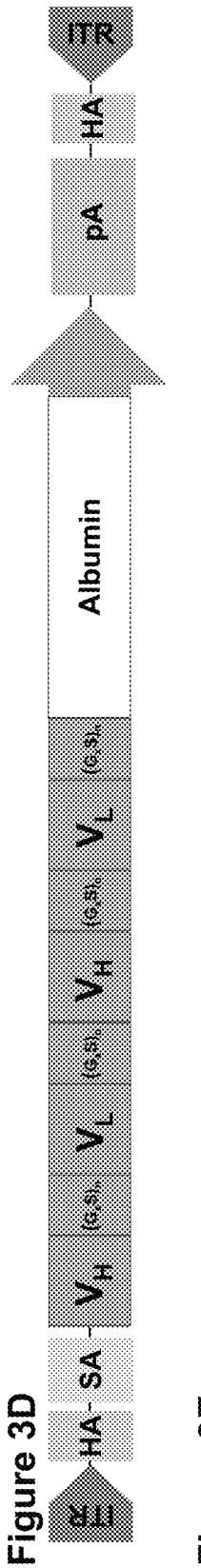
Figure 3E:
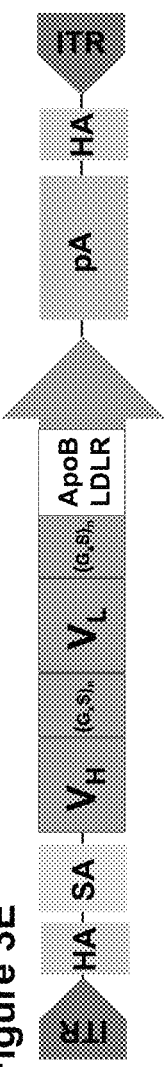
Figure 4:
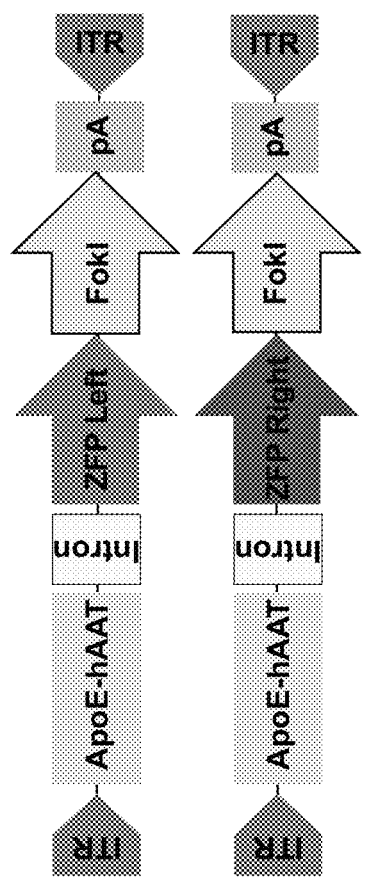
FIG. 4 shows schematics depicting nuclease designs. Design of separate vectors for each ZFN of the pair used for safe harbor cleavage for targeted integration of antibody donors. "ApoE-hAAT" refers to the hAAT promoter fused to the ApoE enhancer sequence. All other abbreviations are as in FIG. 3.

The C6.5 antibody donor constructs were based on Genbank sequences U36542.1 for the human anti-c-erbB-2 immunoglobulin heavy chain V region, and U36541.1 for the human anti-c-erbB-2 immunoglobulin light chain V region, as well as patent publication WO1997000271. (See also Schier et al. (1995), *Immunotechnology*, 73-81; Schier et al., (1996) *J. Mol. Biol.*, 255, 28-43; Schier et al., (1996) *J Mol. Biol.*, 263, 551-567). Overall C6.5 antibody donor architecture was as outlined in FIGS. 2 through 3, with left and right mouse albumin intron homology arms, splice acceptor, poly A, as well as C-terminal myc and Flag epitope tags. For C-terminal mouse serum albumin (MSA) fusions, or C-terminal human serum albumin (HSA) fusions (see FIGS. 3C and 3D), the MSA or HSA was appended after the C-terminal myc-Flag tag. The MSA or HSA encoded the mature albumin coding region (lacking the pro-peptide and signal peptide).

The alpha-synuclein antibody donor constructs were based on: Genbank sequence JX442980.1 for alpha-synuclein D5E single chain antibody; Genbank X0506.1 and Swi-Prot P04114.2 for the human apolipoprotein B-100 low density lipoprotein (ApoB LDL) residues 3371-3409. The alpha-synuclein D5E constructs all had C-terminal myc-Flag tags after the ApoB LDLR, and in one case Flag was replaced with 3x-Flag. The nucleic acid sequence encoding the ApoB LDLR and the resultant amino acid sequence are as follows:

Nucleic Acid Sequence:

(SEQ ID NO: 25)
5'TCATCTGTCATTGATGCACTGCAGTACAAATTAGAGGGCACCACAAGA
TTGACAAGAAAAAGGGGATTGAAGTTAGCCACAGCTCTGTCTCTGAGCAA
CAAATTTGTGGAGGGTAGT

Amino Acid Sequence:

(SEQ ID NO: 26)
N' SSVIDALQYKLEGTTRLTRKRGLKLATALSLSNKFVEGS.

The donors were then packaged into AAV2/6 or AAV2/8 particles per standard techniques.

For detection of the expressed antibodies, the levels of C6.5 antibodies secreted into the Hepa1-6 cellular supernatant or mouse plasma were determined using a custom ELISA taking advantage of the C-terminal myc-Flag tags on the C6.5 antibody donors. 96-well strip plates (Pierce Thermo Fisher Scientific, Waltham Mass.) were coated overnight at 4° C. with mouse monoclonal anti-Flag M2 antibody (Sigma Aldrich, St. Louis Mo.) at 4 µg/mL in 0.2 M carbonate bicarbonate buffer pH 9.4 (Pierce Thermo Fisher Scientific, Waltham Mass.) using 100 µL per well (400 ng/well final).

The following day the plates were washed using 1× TB ST (VWR International, Radnor Pa.). 96-well plates were then blocked two hours at room temperature using blocking buffer (Pierce Thermo Fisher Scientific, Waltham Mass.), followed by washing three times with 1× TB ST. Supernatants from the Hepa1-6 cells (or plasma for in vivo studies) were added to the plate and incubated with rocking at room temperature for two hours, followed by washing three times with 1× TB ST. Rabbit monoclonal myc-Biotin (Cell Signaling Technology, Danvers Mass.) was added (diluted 1:1000 in blocking buffer), incubated for one hour at room temperature, followed by washing three times with 1×TBST. Poly-Streptavidin HRP (Pierce Thermo Fisher Scientific, Waltham Mass.) was added (diluted 1:5000 in blocking buffer, final 100 ng/mL), incubated for one hour at room temperature followed by washing three times with 1×TBST. TMB Ultra (Pierce Thermo Fisher Scientific, Waltham Mass.) was added and allowed to develop for ten minutes, reaction was stopped with stop solution and absorbance read at 450 nM using a plate reader. Background absorbance readings were negligible (typically 0).

Binding of the C6.5 secreted antibodies to the Her2 target was determined using a custom ELISA. 96-well strip plates (Pierce Thermo Fisher Scientific, Waltham Mass.) were coated overnight at 4° C. with Her2 extracellular domain (ECD) residues 23-652 (Novus Biologicals, Littleton Colo.) at 1 ug/mL in 0.2 M carbonate bicarbonate buffer pH 9.4 (Pierce Thermo Fisher Scientific, Waltham Mass.) using 100 µL per well (100 ng/well final). The following day plates were washed using 1× TB ST (VWR International, Radnor Pa.). 96-well plates were then blocked one and a half hours at room temperature using blocking buffer (Pierce Thermo Fisher Scientific, Waltham Mass.), followed by washing three times with 1×TBST. Supernatants from the Hepa1-6 cells were added to the plate and incubated with rocking at room temperature for two hours, followed by washing three times with 1×TBST. Rabbit monoclonal myc-Biotin (Cell Signaling Technology, Danvers Mass.) was added at 1:1000 dilution in blocking buffer, incubated for one hour at room temperature, followed by washing three times with 1× TBST. Poly-Streptavidin HRP (Pierce Thermo Fisher Scientific, Waltham Mass.) was added (diluted 1:5000 in blocking buffer, final 100 ng/mL), incubated for one hour at room temperature followed by washing three times with 1×TBST. TMB Ultra (Pierce Thermo Fisher Scientific, Waltham Mass.) was added and allowed to develop for ten minutes, reaction was stopped with stop solution and absorbance read at 450 nM using a plate reader. Background absorbance readings were negligible (typically 0).

For in vitro studies, mouse Hepa1-6 cells were maintained per manufacturer's guidelines (ATCC, Manassas Va.). On the day of the experiment, Hepa1-6 cells were washed, trypsinized and counted. ZFNs used were to mouse albumin intron locus, left SBS48641 and right SBS31523. ZFN mRNA was transcribed in vitro using mMessage Machine Kit according to the manufacturer's recommendations (Ambion, Thermo Fisher Scientific, Waltham Mass.). ZFNs were delivered as mRNA either by electroporation (Amaxa Lonza, Walkersville Md.), or transfection (Lipofectamine 2000, Invitrogen Thermo Fisher Scientific, Waltham Mass.) followed shortly thereafter by addition of AAV2/6 C6.5 antibody donors, denoted as time zero. Typical reactions used were 25-200 ng of ZFN mRNA and AAV2/6 C6.5 antibody donors MOI of 60K-2400K for 2E+05 cells per well of a 24-well dish. The following day media was exchanged. Supernatants were analyzed for secreted C6.5 antibodies using the Levels and/or Her2 binding ELISAs described above at various time points ranging from t4 to t10 days post-ZFN mRNA and AAV2/6 donor addition.

Figure 5A:
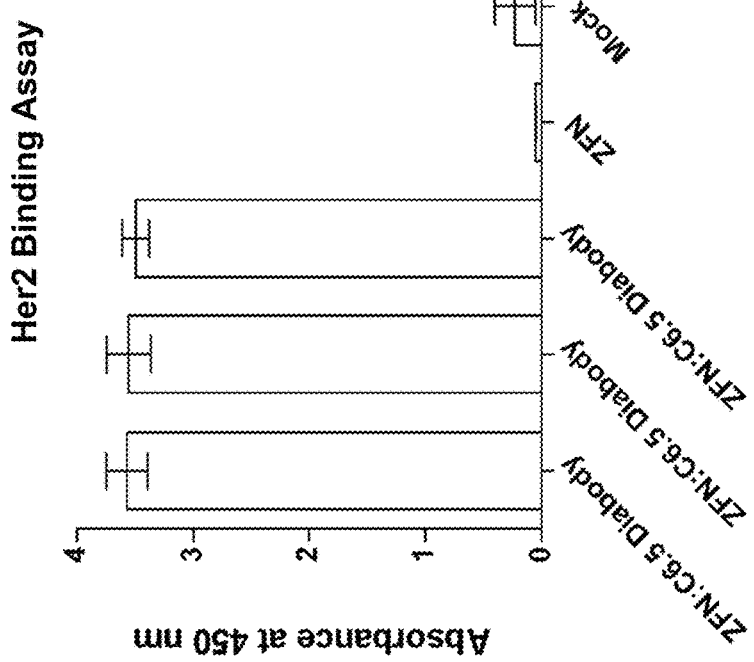
FIGS. 5A and 5B depict graphs showing the in vitro production of engineered antibodies following targeted integration of the indicated antibody-encoding transgene donors into the endogenous albumin locus.
Figure 5B:
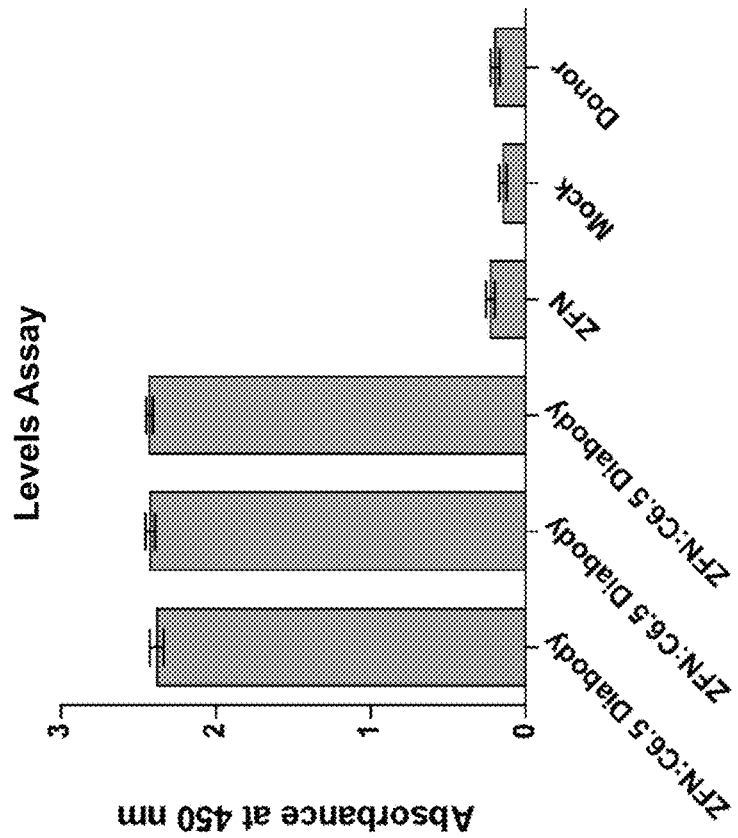
Figure 6B:
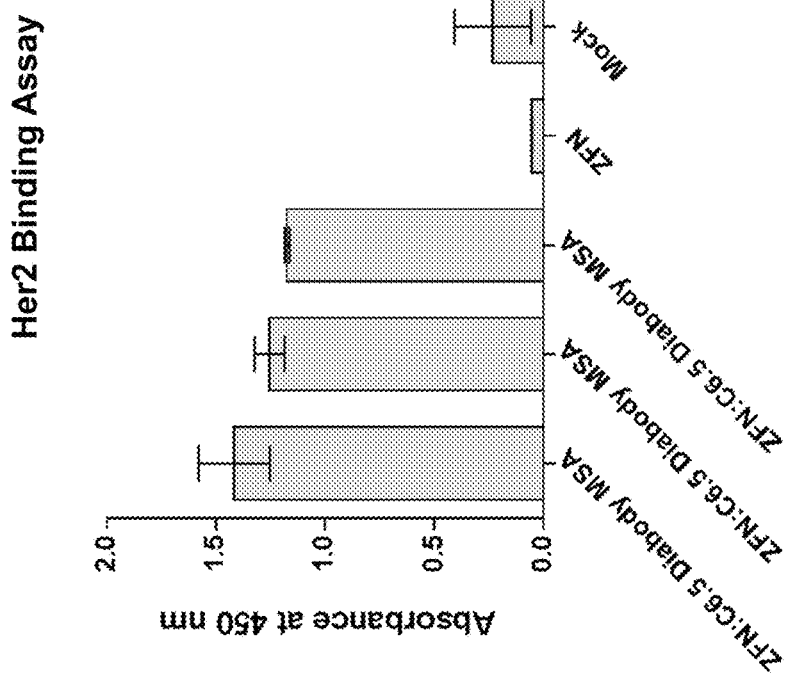
FIGS. 6A and 6B are graphs showing the in vitro production of engineered antibody-albumin fusions following nuclease-mediated integration of the indicated antibody-encoding transgene into the endogenous albumin locus.
Figure 6A:
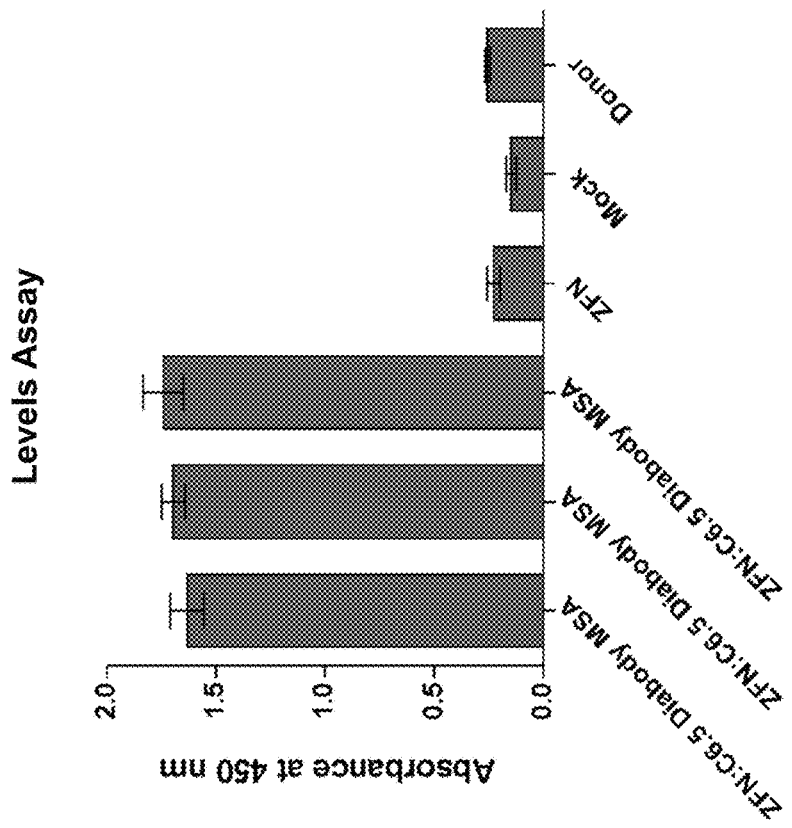
Figure 9:
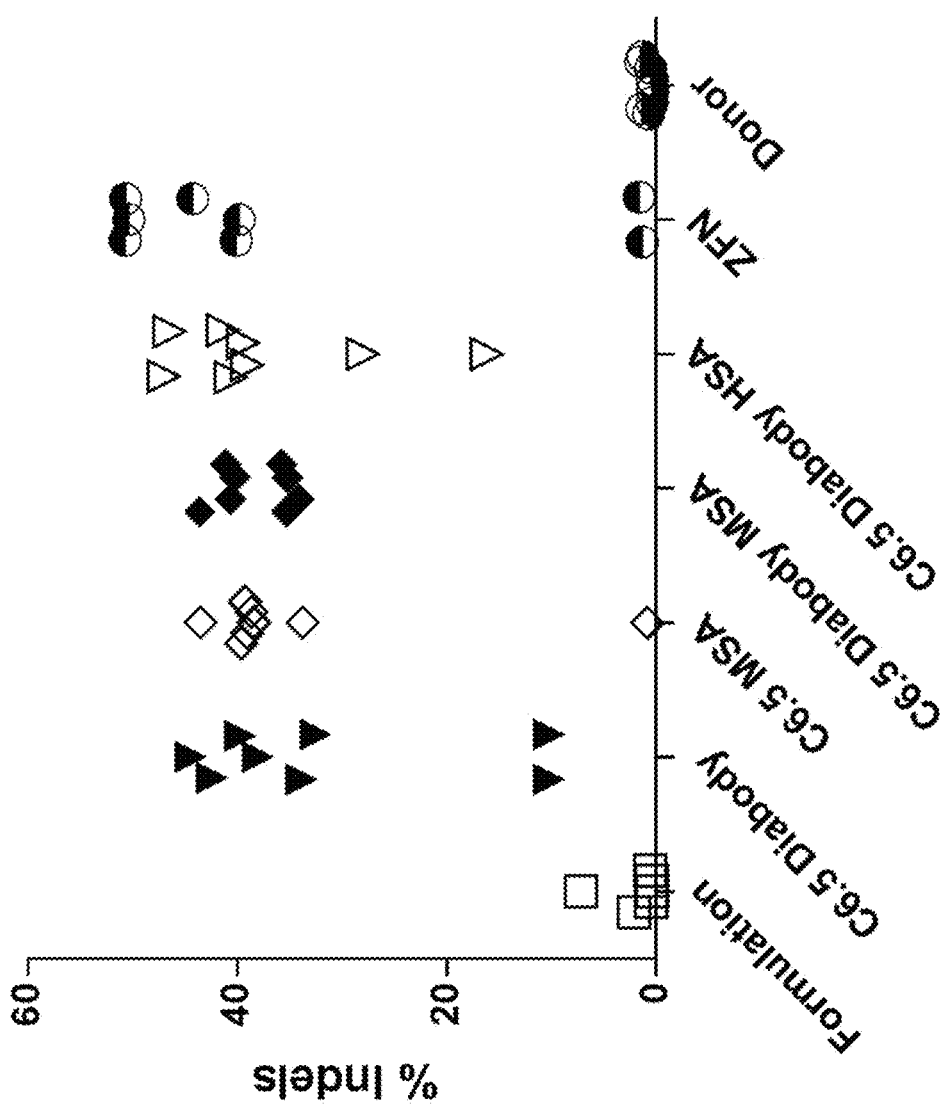
FIG. 9 is a graph depicting levels of in vivo gene modification (% Indels) following in vivo nuclease-mediated introduction of the indicated antibody-encoding transgene donors. The data shown reflects % Indels for the mouse study 28 days post-test article administration.
Figure 10:
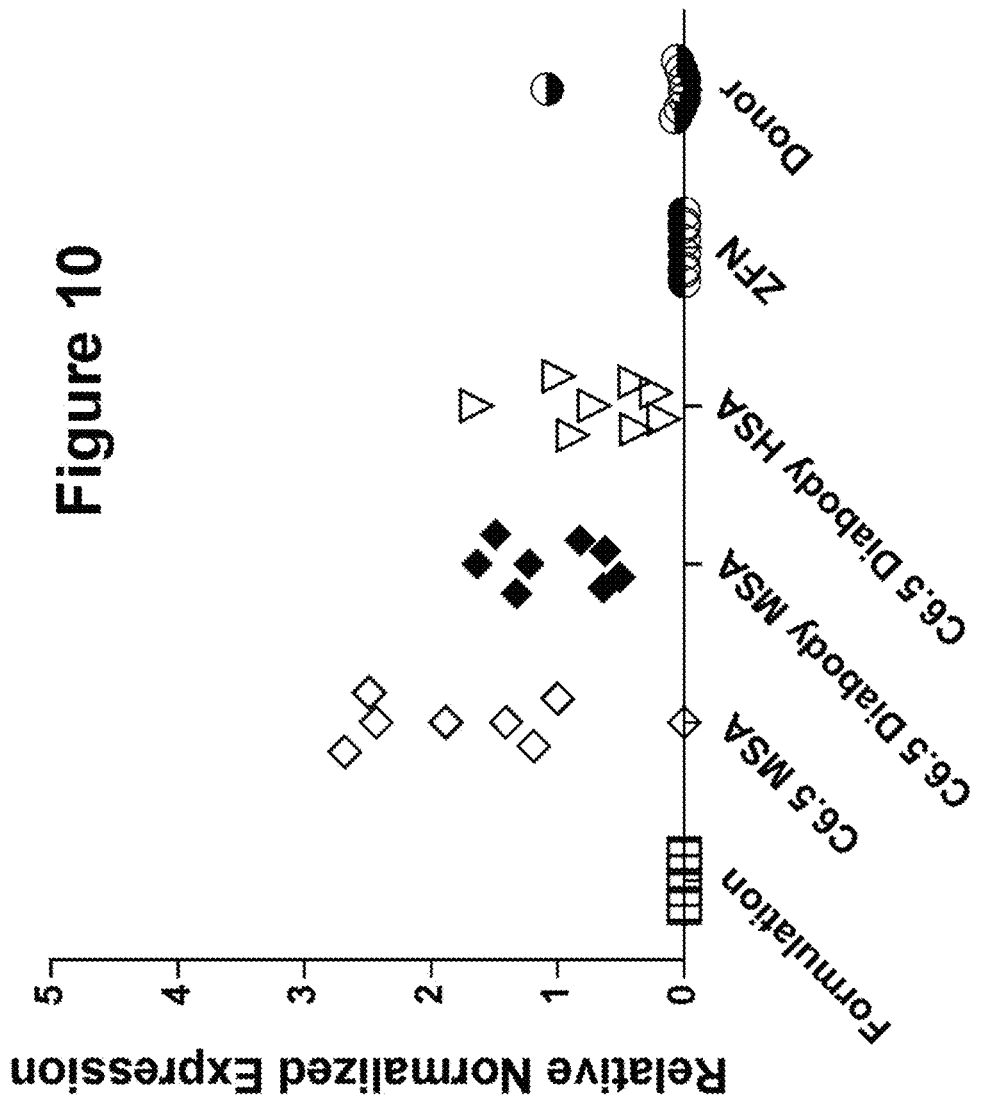
FIG. 10 is a graph depicting levels of in vivo endogenous albumin-engineered antibody transcript following in vivo nuclease-mediated introduction of the indicated antibody-encoding transgene donors, where the levels of endogenous albumin-C6.5 mRNA were assayed by quantitative RT-PCR. The 5' primer and probe are located within the endogenous mouse albumin locus, and the 3' primer within the engineered antibody donor.

The results are depicted in FIGS. 5, 6, and 7, where FIG. 5 shows the antibodies produced as antibody alone, and FIG. 6 shows the antibodies produced as scFv-albumin or diabody-albumin fusion proteins. FIG. 7 depicts the successful expression of the anti-synuclein antibodies in this system. The results demonstrate that antibodies were expressed from the albumin locus in these cells and secreted into the cell media.

For the in vivo studies, eight to ten week old C57BL/6 mice were used and administered nucleases and transgene ("test articles" denoted in FIG. 11). The study complied with the animal welfare act for humane care and use of animals. Test articles were thawed at room temperature prior to dosing, and all animals received a single intravenous (IV) 200 μL injection as outlined in FIG. 11. ZFNs used were to mouse albumin intron locus, left SBS48641 and right SBS31523 (Table 1 above). The C6.5 antibody donors are outlined in FIG. 11, and assembly of these constructs described above. Doses were 1:1:8 (ZFN:ZFN:Donor) with 1.5E+11 used for each ZFN and 1.2E+12 used for the donor, all AAV2/8 virus. All animals received a follow-up 200 μL intraperitoneal injection of cyclophosphamide on Days 0 and 14. Non-terminal and terminal blood collections were done as outlined in Table 5 below, with the processing procedure described below.

TABLE 5

Schedule of bleeds

Serial Bleed Day - Plasma (Number of Mice/Time Point)

| Group | 7 | 14 | 17 | 21 | 24 | 27 | 28 |
|---|---|---|---|---|---|---|---|
| 1 | 6 | 3 |   | 3 |   | 3 | 6 |
|   |   |   | 3 |   | 3 |   |   |
| 2 | 8 | 4 |   | 4 |   | 4 | 8 |
|   |   |   | 4 |   | 4 |   |   |
| 3 | 8 | 4 |   | 4 |   | 4 | 8 |
|   |   |   | 4 |   | 4 |   |   |
| 4 | 8 | 4 |   | 4 |   | 4 | 8 |
|   |   |   | 4 |   | 4 |   |   |
| 5 | 8 | 4 |   | 4 |   | 4 | 8 |
|   |   |   | 4 |   | 4 |   |   |
| 6 | 8 | 4 |   | 4 |   | 4 | 8 |
|   |   |   | 4 |   | 4 |   |   |
| 7 | 8 | 4 |   | 4 |   | 4 | 8 |
|   |   |   | 4 |   | 4 |   |   |

Plasma—Blood was collected from all mice on Days 7 (non-terminal) and Day 28 (terminal). Blood was collected from three (3) mice in Group 1 and from four (4) mice in Groups 2-7 on Days 14, 21, and 27. Blood was collected from the remaining three (3) mice in Group 1 and from the remaining four (4) mice in Groups 2-7 on Days 17 and 24. All blood was collected into tubes containing sodium citrate and processed to plasma. Non-terminal blood collections were collected via the submandibular vein or the retro-orbital sinus. Blood collections at the time of sacrifice were collected via cardiac puncture or vena cava. The plasma was separated and stored at −60 to −80° C. until use in the ELISA assay described above.

Liver—All animals were sacrificed at Day 28 and the liver and spleen were collected and weighed. The left lateral lobe of the liver was separated and divided into three pieces and snap frozen in liquid nitrogen separately from the rest of the liver. The remaining liver lobes and spleen (whole) were snap frozen in liquid nitrogen. Frozen specimens were stored at −60 to −80° C. until processing for RNA/DNA extraction.

The results (see FIG. 8) demonstrated that recombinant anti-Her2 antibodies were detectable in the serum of the mice. The liver tissue was also studied to determine the amount of genome alteration (measured as indels, which can include NHEJ activity as well as integration of the donor sequences), and showed that in mice that received both the engineered nuclease and the donor DNA, indels were present at levels up to approximately 50%.

Thus, the antibody-encoding transgenes were expressed following in vivo administration.

Example 4

In Vivo Studies

A. Methods

Mice: The Line 61 alpha-synuclein transgenic mouse model is characterized by overexpression of human alpha-synuclein driven by the Thy1 promoter in all brain regions. Strain background is C57BL/6 and DBA. Mice from Line 61 develop intraneuronal alpha-synuclein inclusions distributed throughout the brain similar to those observed in brains of patients with Parkinson's Disease (PD) and Diffuse Lewy Body disease (DLB).

Approximately 2-3 month old Line 61 alpha-synuclein transgenic mice were used for the in vivo study (test articles denoted in Table 6).

TABLE 6

Group Designations and Dose Levels

| Group No. | Test Article | Test Article Description | No. of Animals | Genotype | ZFN Each Dose Level (vg/mouse) | cDNA or Donor Dose Level (vg/mouse) | Total Dose (vg/mouse) |
|---|---|---|---|---|---|---|---|
| 1 | 16EXP002-01 | Formulation Test Article 1 | 6 | Line 61 | — | — | — |
| 2 | 16EXP002-02 | Positive Control Test Article 2 | 6 | Line 61 | — | NA | NA |
| 3 | 16EXP002-03 | D5E cDNA Test Article 3 | 8 | Line 61 | — | 1.8E+11 | 1.8E+11 |
| 4 | 16EXP002-04 | D5E GBA cDNA Test Article 4 | 8 | Line 61 | — | 1.8E+11 | 1.8E+11 |
| 5 | 16EXP002-05 | ZFN + D5E Donor Test Article 5 | 8 | Line 61 | 1.5E+11 | 1.2E+12 | 1.5E+12 |
| 6 | 16EXP002-06 | ZFN + D5E GBA Donor Test Article 6 | 8 | Line 61 | 1.5E+11 | 1.2E+12 | 1.5E+12 |

The study complied with the animal welfare act for humane care and use of animals. Test articles were thawed at room temperature prior to dosing, and all animals received a single intravenous (IV) 200 μL injection as outlined in Table 6 with the exception of the positive control which was injected IP (intraperitoneal) to reflect the method used by previous studies that used a similar test article (Spencer et al. *Molecular Therapy* 2014).

ZFNs used were to mouse albumin intron locus, left SB S48641 and right SBS31523. See, e.g., US Publication No. 20160060656. The alpha-synuclein D5E ScFv antibody donors and alpha-synuclein D5E ScFv cDNAs are outlined in FIG. 12. Doses were 1:1:8 (ZFN:ZFN:Donor) with 1.5E+11 vg/mouse used for each ZFN and 1.2E+12 vg/mouse used for the donor, all AAV2/8 virus. Doses for the cDNAs were 1.8E+11 vg/mouse. Non-terminal and terminal blood collections were done as outlined in Table 7. VG denotes vector genomes. The positive control was based on the test article used in Snencer et al ibid.

TABLE 7

Serial Bleeds Collection Schedule

| | | N/Time point for serial blood collection | | | |
|---|---|---|---|---|---|
| Group No. | Test Article | Day 7 | Day 21 | Day 28 | Day 42 | Day 56 End of Study |
| 1 | Formulation Test Article 1 | 6 | 6 | 6 | 4 | 4 |
| 2 | Positive Control Test Article 2 | 6 | 6 | 6 | 4 | 4 |
| 3 | D5E cDNA Test Article 3 | 8 | 8 | 8 | 6 | 6 |
| 4 | D5E GBA cDNA Test Article 4 | 8 | 8 | 8 | 6 | 6 |
| 5 | ZFN + D5E Donor Test Article 5 | 8 | 8 | 8 | 6 | 6 |
| 6 | ZFN + D5E GBA Donor Test Article 6 | 8 | 8 | 8 | 6 | 6 |

Immunostaining: Following mouse sacrifice, brains were removed, split sagitally with half flash frozen and half fixed in 4% paraformaldehyde. The fixed brains were sectioned with a vibratome at 40 μm thickness and probed with anti-α-synuclein (SYN1), anti-GFAP, anti-NeuN or anti-myc (to detect the engineered alpha-synuclein D5E antibodies). Sections were imaged with a Zeiss Imager A2 and optical density was determined with the Zeiss Zen software. For co-immunofluorescence, a Zeiss Axio Imager M2 was used for confocal analysis with a 0.23 μm optical section. For each mouse, a total of three sections were analyzed, and for each section, three fields were examined. All sections were processed simultaneously under the same conditions to reduce variability.

Plasma collection: Non-terminal and terminal blood collections were performed as outlined in Table 6. Non-terminal blood (~50-100 μL) was collected from mice on Days 7, 21, 28, 42, 56. Terminal blood was collected on Day 28 (for Cohort 1) and Day 56 (for Cohort 2). All blood was collected into tubes containing K2-EDTA (purple tubes) and processed to plasma. Non-terminal blood collections were collected via mandibal. Blood collections at the time of sacrifice were collected via manidibal (200-500 uL). Plasma, which will be approximately half the blood collected, was stored at −60° C. to −80° C. and used to measure circulating alpha-synuclein single chain antibody levels. Plasma volumes for non-terminal collections were approximately 50-100 μL and were snap frozen prior to storage at −60° C. to −80° C.

Perecentage (%) Indels (insertions and/or deletions): Mouse tissue was lysed using FastPrep and Lysing Matrix D (MP Biomedicals, Santa Ana Calif.) per the manufacturer's instructions. RNA/DNA was isolated from mouse tissue using AllPrep DNA/RNA kit per the manufacturer's instructions (Qiagen, Carlsbad Calif.). Extracted DNA was used for PCR and deep sequencing to measure indels at the mouse albumin locus. Table 8 shows Cohort 1 (Sacrifice Day 28) and Cohort 2 (Sacrifice Day 56).

TABLE 8

Cohort 1 (Sacrifice Day 28) and Cohort 2 (Sacrifice Day 56)

| | | N/Time point for serial blood collection | | | |
|---|---|---|---|---|---|
| Group No. | Test Article | Day 7 | Day 21 | Day 28 | Day 42 | Day 56 End of Study |
| 1 | Formulation Test Article 1 | 6 | 6 | 6 | 4 | 4 |
| 2 | Positive Control Test Article 2 | 6 | 6 | 6 | 4 | 4 |
| 3 | D5E cDNA Test Article 3 | 8 | 8 | 8 | 6 | 6 |
| 4 | D5E GBA cDNA Test Article 4 | 8 | 8 | 8 | 6 | 6 |
| 5 | ZFN + D5E Donor Test Article 5 | 8 | 8 | 8 | 6 | 6 |
| 6 | ZFN + D5E GBA Donor Test Article 6 | 8 | 8 | 8 | 6 | 6 |

B. Results

Figure 13B:
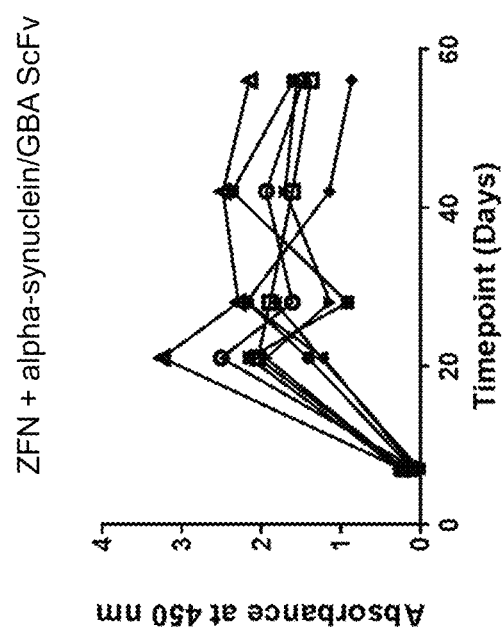
FIGS. 13A and 13B are graphs depicting in vivo production of engineered alpha-synuclein single chain antibodies following targeted integration into the endogenous albumin locus.
Figure 13A:
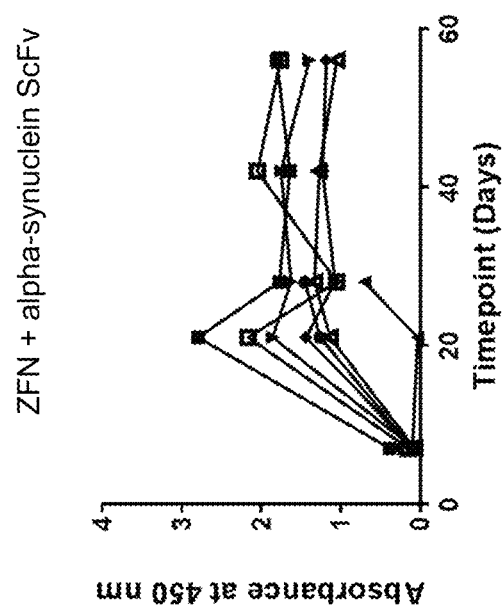
Figures 14A, 14B:
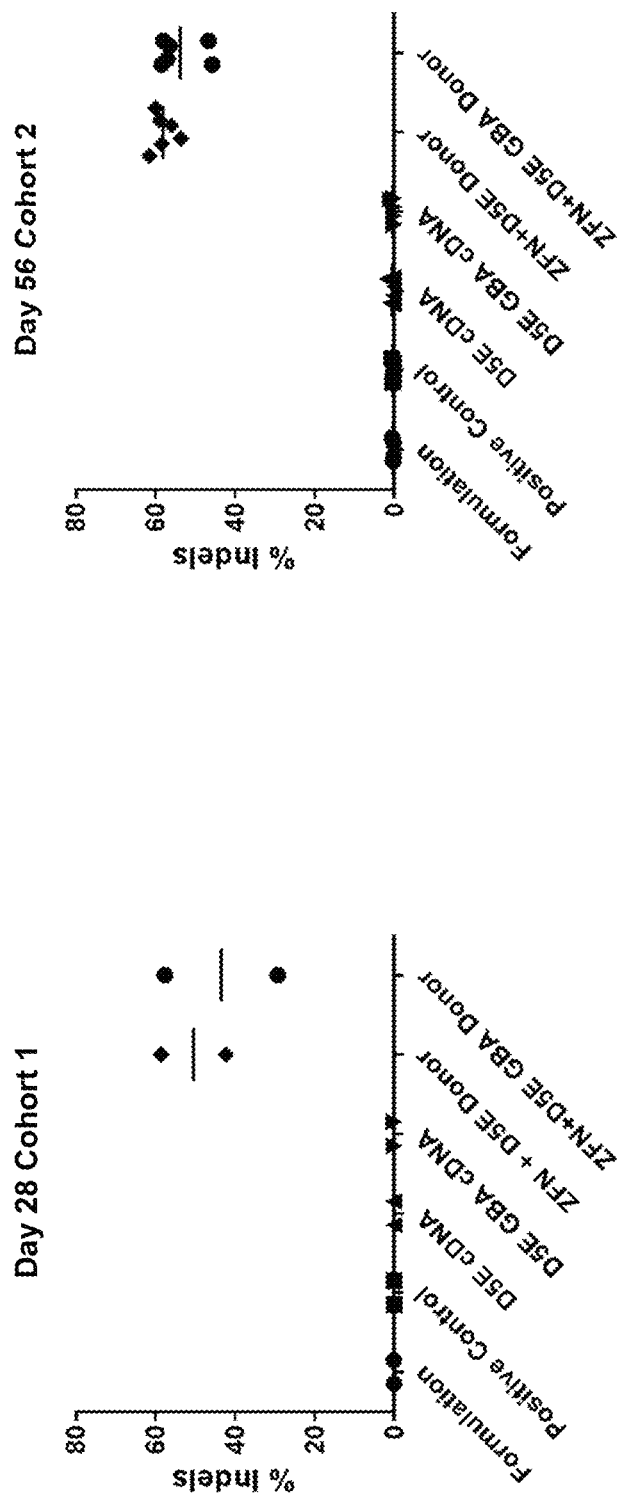
FIGS. 14A and 14B are graphs depicting levels of in vivo gene modification (% Indels).

As shown in FIG. 13, circulating plasma levels of the alpha-synuclein D5E antibody following in vivo administration of albumin-targeted ZFNs and the alpha-synuclein D5E antibody-encoding donor to mice increased in all treated subjects. In addition, genomic modification (as determined by % Indels) was seen in subjects receiving both the ZFNs and alpha synuclein donors at 28 days and 56 days. See, FIG. 14.

Figure 16A:
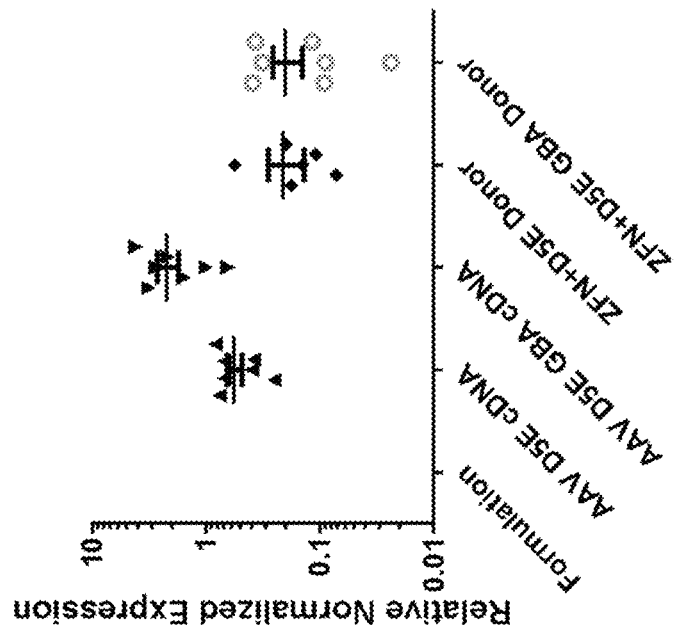
FIGS. 16A and 16B are graphs depicting in vivo levels of D5E (+/−GBA) antibody transcript.
Figure 16B:
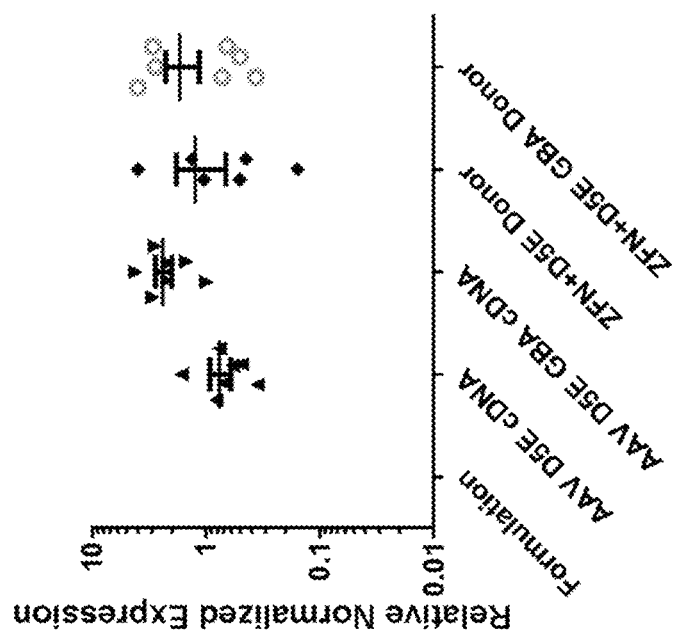
Figure 17B:
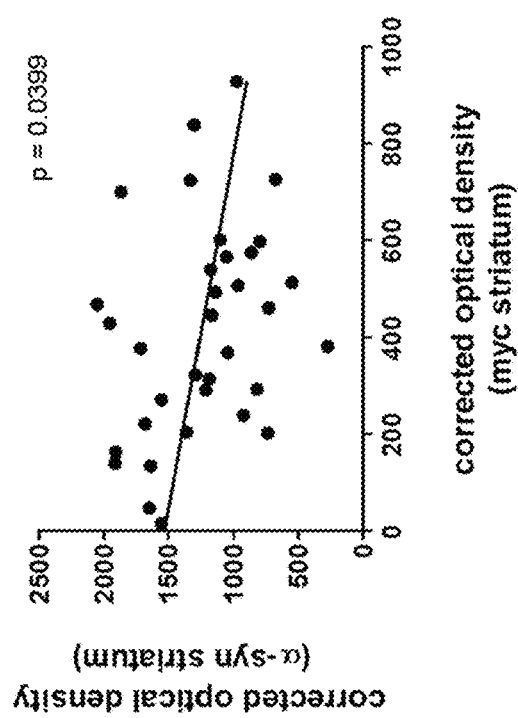
FIGS. 17A and 17B are graphs showing the correlation between antibody levels and reduced alpha-synuclein in the cortex neuropil and striatum.
Figure 17A:
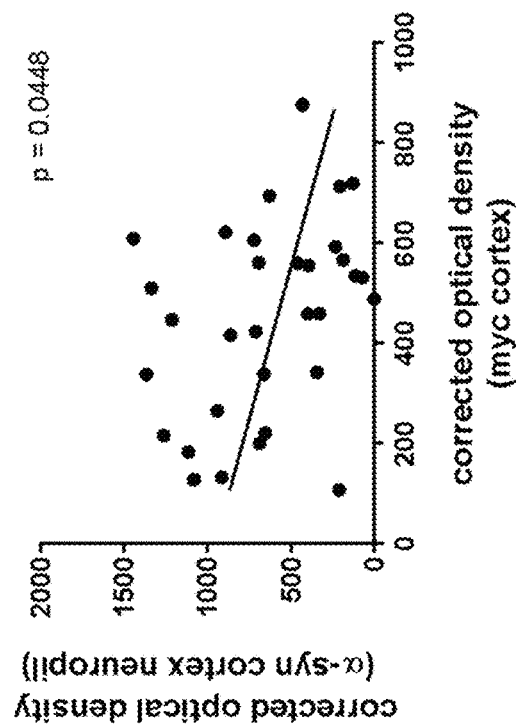
Figure 18B:
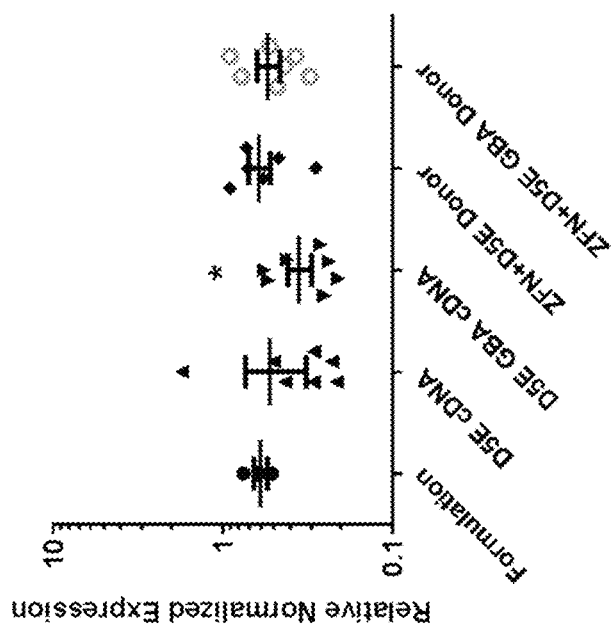
FIGS. 18A and 18B are graphs showing reduction in CNS accumulation of alpha-synuclein positive cells and the astrogliosis marker GFAP.
Figure 18A:
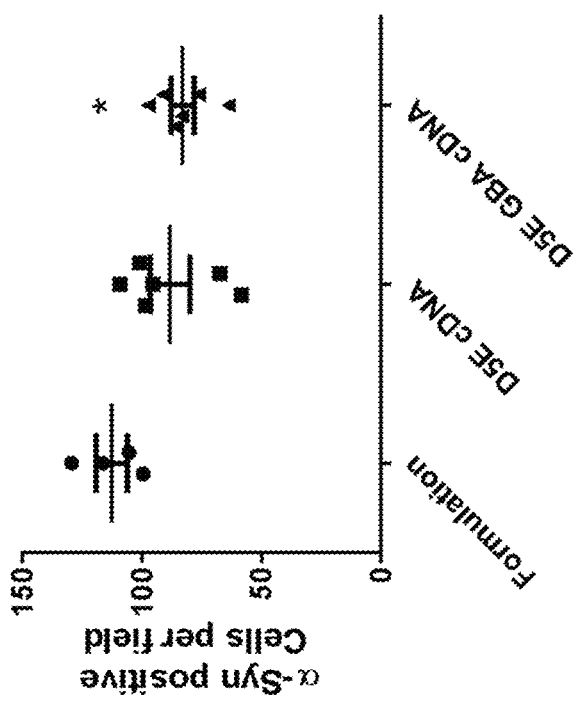

Immunohistochemistry showed the uptake of alpha-synuclein single chain antibodies by neurons in the thalamus. In particular, double immunofluorescence staining of the thalamus from alpha-synuclein transgenic line 61 mice with myc to detect the alpha-synuclein single chain antibodies (ScFv are myc-tagged), and NeuN showed the neurons of the ZFN-alpha synuclein donor included both the alpha-synuclein ScFv (positive for myc) and NeuN. In addition, as shown in FIG. 15, mice with albumin-targeted alpha-synuclein donors showed reduction in the astrogliosis disease endpoint, GFAP. FIG. 16 shows increased in vivo levels of D5E (+/−GBA) antibody transcript in liver as determined by quantitative RT-PCR and FIG. 17 shows the correlation between antibody levels and reduced alpha-synuclein levels in the cortex neuropil and striatum. FIG. 18 shows reduction in CNS accumulation of alpha-synuclein positive cells of the astrogliosis marker GFAP and a reduction in the total number of alpha-synuclein positive neurons in the cortex in the D5E GBA antibody cDNA-treated group. Thus, addition of the genes encoding the ScFV are able to be expressed and excreted from the liver cells and travel to the brain and provide therapeutic benefit.

Thus, targeted delivery of antibody (e.g., single chain antibodies) transgenes as described herein provides clinical (therapeutic) benefits in vivo.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of expressing, in a mammalian liver cell, an antibody, wherein the antibody binds to a protein expressed in the brain, wherein the protein is selected from the group consisting of a cancer antigen, a cellular receptor, a cytokine, a growth factor, a growth factor receptor, a kinase inhibitor, an integrin, α-synuclein, an amyloid protein, and a complement protein, the method comprising, administering to the liver cell (i) an adeno-associated viral (AAV) vector comprising a transgene encoding the antibody, wherein the antibody is a single chain fragment variable (ScFv), an intrabody or a diabody and (ii) one or more AAV vectors comprising sequences encoding a pair of zinc finger nucleases that cleave an endogenous albumin gene in the liver cell, such that the transgene is integrated into the liver cell and the liver cell produces and secretes the antibody such that the antibody is taken up by neurons in the brain.

2. The method of claim 1, wherein expression of the transgene is driven by the endogenous albumin promoter.

3. The method of claim 1, wherein the transgene is a fusion protein comprising amino acids encoded by the transgene and by the endogenous albumin gene.

4. The method of claim 1, wherein the antibody is expressed in the serum and/or brain of the subject.

5. The method of claim 1, wherein the AAV vector is an AAV2 vector.

6. The method of claim 5, wherein the AAV2 vector is an AAV2/6 or AAV2/8 vector.

7. A genetically modified liver cell produced by the method of claim 1.

* * * * *

```
                             SEQUENCE LISTING

<160> NUMBER OF SEQ ID NOS: 27

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Asp Asn Leu Ser Glu
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ser Gly Asn Leu Ala Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Arg Ser Asn Leu Ser Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Arg Ser Ser Leu Arg Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ser Ser Asp Arg Lys Lys
1               5
```

```
<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Ser Gly Ser Leu Thr Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Asp Ala Leu Ser Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ser Ala Thr Arg Thr Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Arg His His Leu Thr Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ala Gly Gln Arg Arg Val
1               5

<210> SEQ ID NO 11
<211> LENGTH: 28
<212> TYPE: DNA
<213> ORGANISM: Mus sp.

<400> SEQUENCE: 11
tttcctgtaa cgatcgggaa ctggcatc                                    28
```

```
<210> SEQ ID NO 12
<211> LENGTH: 28
<212> TYPE: DNA
<213> ORGANISM: Mus sp.

<400> SEQUENCE: 12
ctgaaggtgg caatggttcc tctctgct                                          28

<210> SEQ ID NO 13
<211> LENGTH: 23
<212> TYPE: DNA
<213> ORGANISM: Homo sapiens

<400> SEQUENCE: 13
taattttctt ttgcgcacta agg                                               23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtaattttct tttgcgcact a                                                 21

<210> SEQ ID NO 15
<211> LENGTH: 23
<212> TYPE: DNA
<213> ORGANISM: Homo sapiens

<400> SEQUENCE: 15
tgactgaaac ttcacagaat agg                                               23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtgactgaaa cttcacagaa t                                                 21

<210> SEQ ID NO 17
<211> LENGTH: 23
<212> TYPE: DNA
<213> ORGANISM: Homo sapiens

<400> SEQUENCE: 17
gactgaaact tcacagaata ggg                                               23

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gactgaaact tcacagaata                                                   20
```

<210> SEQ ID NO 19
<211> LENGTH: 23
<212> TYPE: DNA
<213> ORGANISM: Homo sapiens

<400> SEQUENCE: 19
tagtgcaatg gataggtctt tgg                                              23

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtagtgcaat ggataggtct t                                                21

<210> SEQ ID NO 21
<211> LENGTH: 23
<212> TYPE: DNA
<213> ORGANISM: Homo sapiens

<400> SEQUENCE: 21
taaagcatag tgcaatggat agg                                              23

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtaaagcata gtgcaatgga t                                                21

<210> SEQ ID NO 23
<211> LENGTH: 23
<212> TYPE: DNA
<213> ORGANISM: Homo sapiens

<400> SEQUENCE: 23
gatcaacagc acaggttttg tgg                                              23

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gatcaacagc acaggttttg                                                  20

<210> SEQ ID NO 25
<211> LENGTH: 117
<212> TYPE: DNA
<213> ORGANISM: Homo sapiens

<400> SEQUENCE: 25
tcatctgtca ttgatgcact gcagtacaaa ttagagggca ccacaagatt gacaagaaaa      60

```
aggggattga agttagccac agctctgtct ctgagcaaca aatttgtgga gggtagt            117

<210> SEQ ID NO 26
<211> LENGTH: 39
<212> TYPE: PRT
<213> ORGANISM: Homo sapiens

<400> SEQUENCE: 26

Ser Ser Val Ile Asp Ala Leu Gln Tyr Lys Leu Glu Gly Thr Thr Arg
1               5                   10                  15

Leu Thr Arg Lys Arg Gly Leu Lys Leu Ala Thr Ala Leu Ser Leu Ser
            20                  25                  30

Asn Lys Phe Val Glu Gly Ser
        35

<210> SEQ ID NO 27
<211> LENGTH: 9
<212> TYPE: PRT
<213> ORGANISM: Unknown
<220> FEATURE:
<223> OTHER INFORMATION: Description of Unknown: Naturally-occurring
      meganuclease peptide

<400> SEQUENCE: 27

Leu Ala Gly Leu Ile Asp Ala Asp Gly
1               5
```